US009416151B2

(12) United States Patent
Zhang et al.

(10) Patent No.: US 9,416,151 B2
(45) Date of Patent: Aug. 16, 2016

(54) USE OF GLYCYRRHETINIC ACID, GLYCYRRHIZIC ACID AND RELATED COMPOUNDS FOR PREVENTION AND/OR TREATMENT OF PULMONARY FIBROSIS

(75) Inventors: Lurong Zhang, Gainesville, FL (US); Weijian Zhang, Fujian (CN); Jianhua Xu, Fujian (CN); Shanmin Yang, Gainesville, FL (US)

(73) Assignee: Lurong Zhang, Gainesville, FL (US)

( * ) Notice: Subject to any disclaimer, the term of this patent is extended or adjusted under 35 U.S.C. 154(b) by 0 days.

(21) Appl. No.: 12/862,980

(22) Filed: Aug. 25, 2010

(65) Prior Publication Data

US 2012/0053141 A1 Mar. 1, 2012

(51) Int. Cl.
*C07H 15/24* (2006.01)
*A61K 31/215* (2006.01)
*A61K 31/16* (2006.01)
*A61K 31/7034* (2006.01)
*A61K 31/19* (2006.01)

(52) U.S. Cl.
CPC .............. *C07H 15/24* (2013.01); *A61K 31/16* (2013.01); *A61K 31/19* (2013.01); *A61K 31/215* (2013.01); *A61K 31/7034* (2013.01)

(58) Field of Classification Search
CPC ... A61K 31/16; A61K 31/19; A61K 31/7034; A61K 31/215; C07H 15/24
USPC .................................. 514/33, 25; 536/4.1, 5
See application file for complete search history.

(56) References Cited

U.S. PATENT DOCUMENTS

| 4,933,169 A | 6/1990 | Shanbrom |
| 6,329,339 B1 | 12/2001 | Pompei et al. |
| 2009/0076032 A1 | 3/2009 | Ward et al. |

FOREIGN PATENT DOCUMENTS

| CN | 100 998 751 A | 7/2007 |
| CN | 101 524 397 A | 9/2009 |
| EP | 0 610 511 | 8/1994 |
| EP | 1 856 973 | 11/2007 |
| JP | 10330256 A | * 12/1998 |
| JP | 2008 222682 A | 9/2008 |
| WO | WO 01/32156 A2 | 5/2001 |

OTHER PUBLICATIONS

He et al. (Zhongguo Yaofang (2006), 17(7), 497-499) (Abstract sent).*
Kureha Chem Ind Co Ltd; JP 10330256 A; Dec. 15, 1998 ( English Machine Translation).*
He et al. (Zhongguo Yaofang (2006), 17(7), 497-499).*
Tabata et al (Am J Respir Crit Care Med vol. 174. pp. 1352-1360, 2006).*
Kao et al. (J. Agric. Food Chem. 2010, 58, 8623-8629).*
Gafoori et al (Oncology, Jan. 1, 2008, pp. 1-4 and 1-9; Review Article, Lung Cancer, Oncology Journal, Palliative and Supportive Care).*
He et al., China Pharmacy, 2009, 19, abstract only, http://en.cnki.com.cn/Article_en/CJFDTOTALZGYA200919007. htm, accessed online on Apr. 4, 2016.*
Roberts et al., Ann. N.Y. Acad. Sci., 2003, 995, p. 1-10.*
Choi, "Radioprotective effect of amifostine in radiation pneumonitis," *Seminars in Oncology*, Dec. 2003, vol. 30, No. 6, Suppl. 18, pp. 10-17.
Tsoutsou et al., "Radiation pneumonitis and fibrosis: mechanisms underlying its pathogenesis and implications for future research," *Int J Radiation Oncology Blot Phys*, 2006, vol. 66, No. 5, pp. 1281-1293.
Vazquez of al., "Protective effect of enriched diet plus growth hormone administration on radiation-induced intestinal injury and on its evolutionary pattern in the rat," Digestive Diseases and Sciences, Nov. 1999, vol. 44, No. 11, pp. 2350-2358.
Lv etal., "Interventional Effect of Glycyrrhizin on Hydroxyproline Acid, and Laminin in Pulmonary Fibrosis Model Rats", *China Pharmacy*, 2008, vol. 19, No. 25, pp. 1954-1955, abstract.
Wang et at, "Experimental Study on Effect of Stronger NEO—Minophagen C in Treating Rats with Bleomycin—induced Pulmonary Fibrosis", *Chinese Archives of Traditional Chinese Medicine*, 2008, vol. 26, No. 12, pp. 2628-2630, abstract.
He, Yan et al., "Antagonistic effect of compound glycyrrhizin on bleomycin-induced pulmonary fibrosis of rats," *Zhongguo Yaofang*, 2006, vol. 17, No. 7, p. 497-499,retrieved from Database CA Chemical Abstract Service, XP-002719057, Abstract only.
Lu, Xiaohua et al., "Interventional effect of glycyrrhizin on hydroxyproline, hyaluronic acid and laminin in pulmonary fibrosis model rats," *Zhongguo Yaofang*, 2008, vol. 19, No. 25, p. 1954-1955, retrieved from Database CA Chemical Abstract Service, XP-002719055, Abstract only.
Ye, Jinyan et al., "Glycyrrhizin inhibits expression of monocyte chemoattractant protein 1 in bleomycin-induced pulmonary fibrosis of rats," *Zhongguo Bingli Shengli Zazhi*, 2007, vol. 23, No. 5, p. 1019-1021, retrieved from Database CA Chemical Abstract Service, XP-002719056, Abstract only.
Menegazzi, Marta et al. "Glycyrrhizin attenuates the development of carrageenan-induced lung injury in mice," *Pharmacol. Res.*, 2008, 58(1):22-31.

* cited by examiner

*Primary Examiner* — Jonathan S Lau
(74) *Attorney, Agent, or Firm* — Saliwanchik, Lloyd & Eisenschenk

(57) ABSTRACT

The present invention pertains to novel uses of glycyrrhetinic acid (GA), glycyrrhizic acid (GLA) and related compounds for prevention and/or treatment of pulmonary fibrosis, in particular, irradiation-induced pulmonary fibrosis. Also embodied are therapeutic uses of prodrugs, metabolites, derivatives (e.g., acids, esters and ethers), and salts of glycyrrhetinic acid (GA) and glycyrrhizic acid (GLA). The present invention also provides for therapeutic or pharmaceutical compositions comprising a compound of the invention in a form that can be combined with a pharmaceutically acceptable carrier.

21 Claims, 27 Drawing Sheets

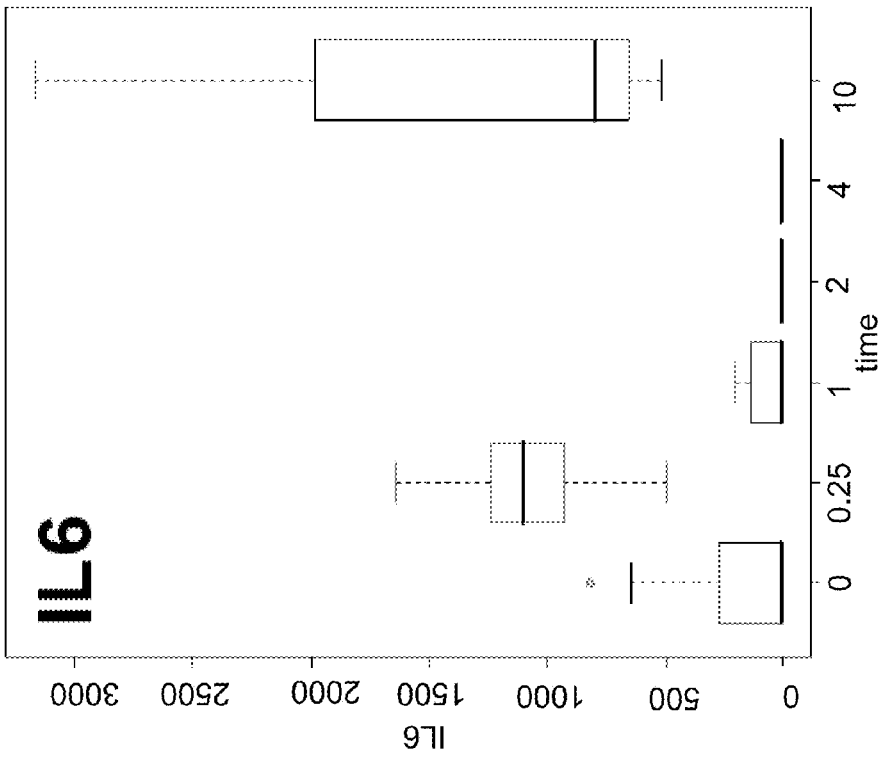
FIG.2A  FIG.2B
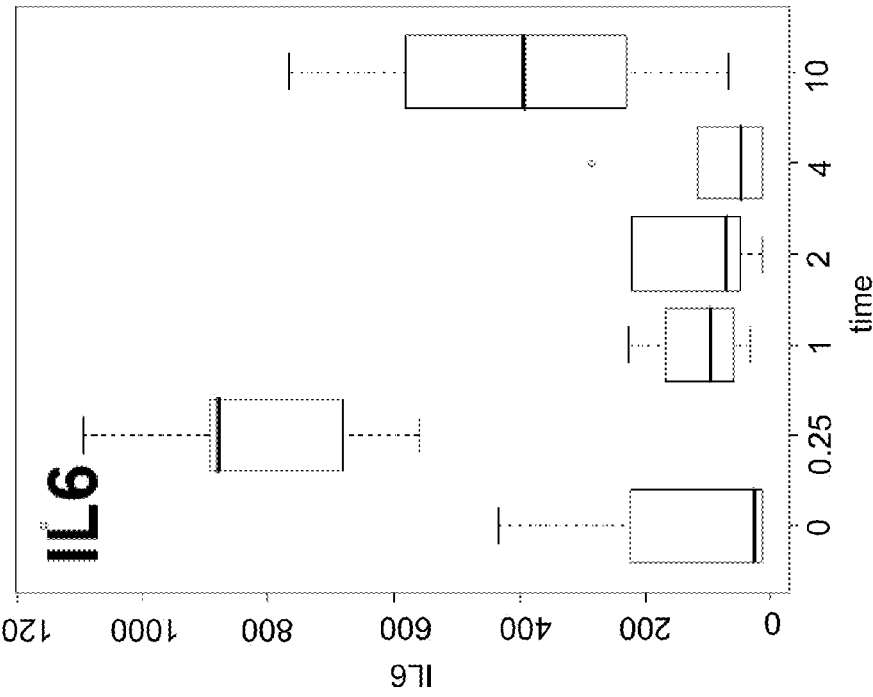

FIG. 10A Effect of GA on Respiratory Rate
(7 months after 15 Gy lung IR)
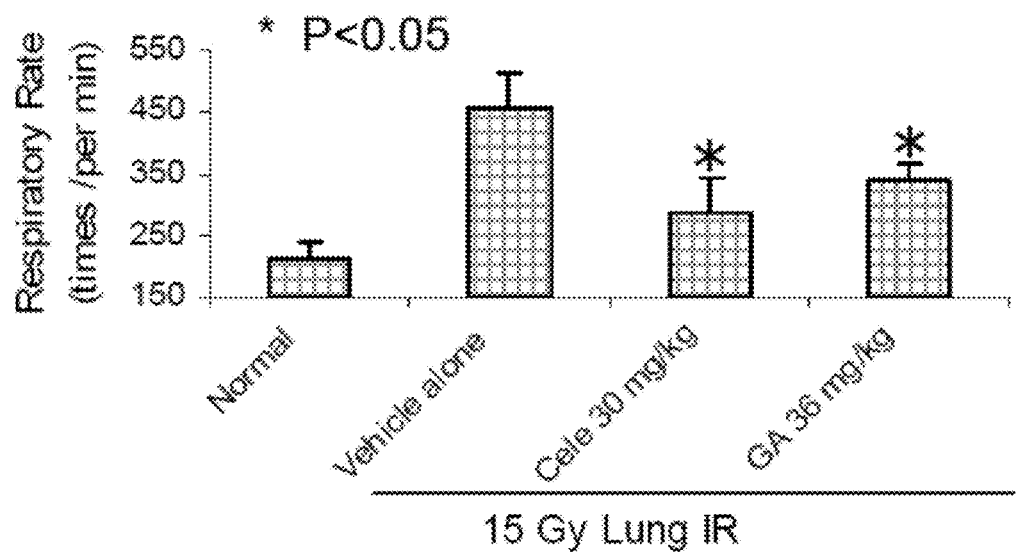
FIG. 10B Effect of GA on Respiratory Rate
(5 months after 18 Gy lung IR)
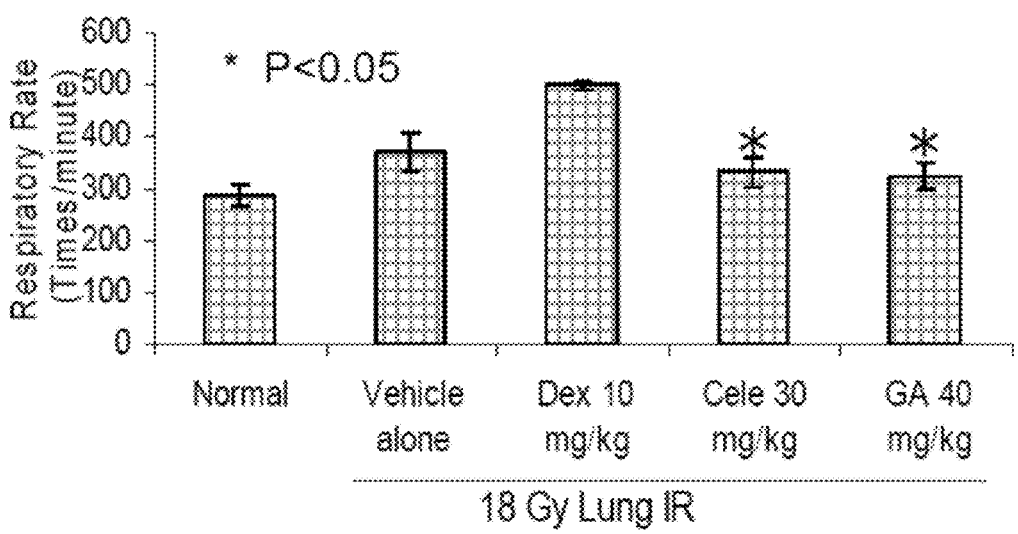

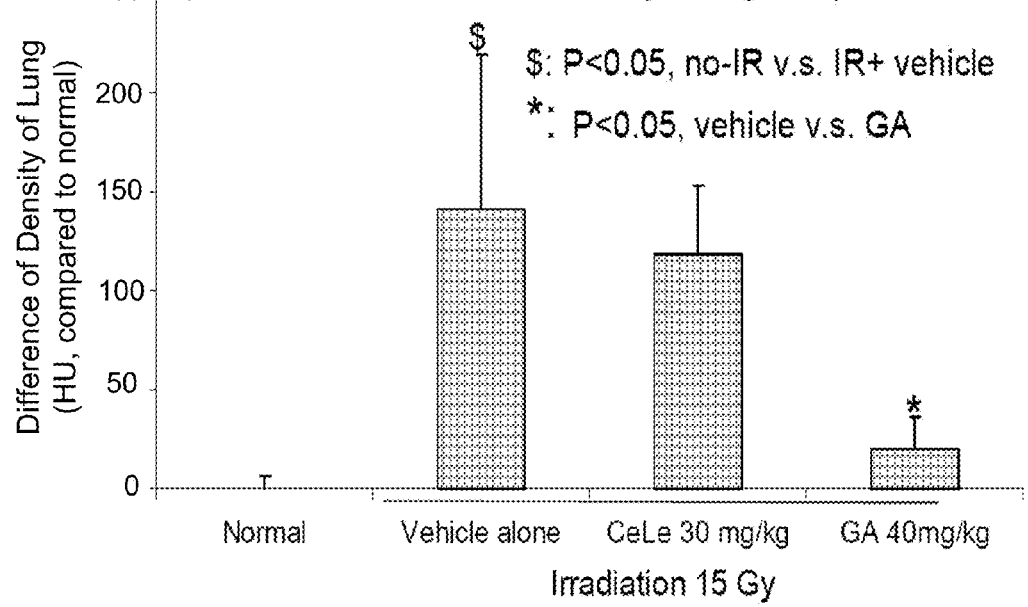
Fig 14 Effect of GA on Lung Density
(7.5 months after 15 Gy lung IR)
$: P<0.05, no-IR v.s. IR+ vehicle
*: P<0.05, vehicle v.s. GA
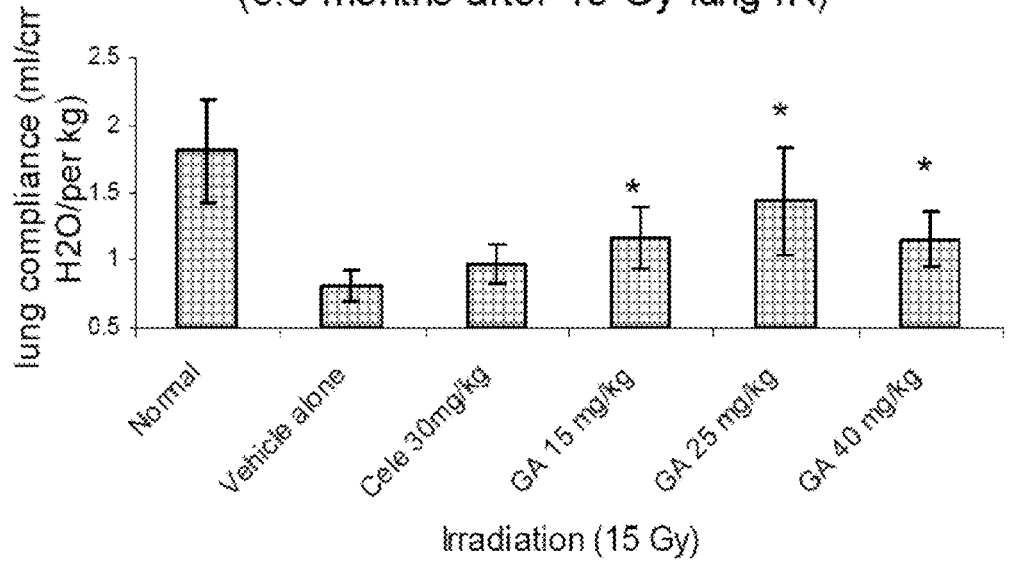
Fig 15 Effect of GA on the Lung Compliance
(6.5 months after 15 Gy lung IR)

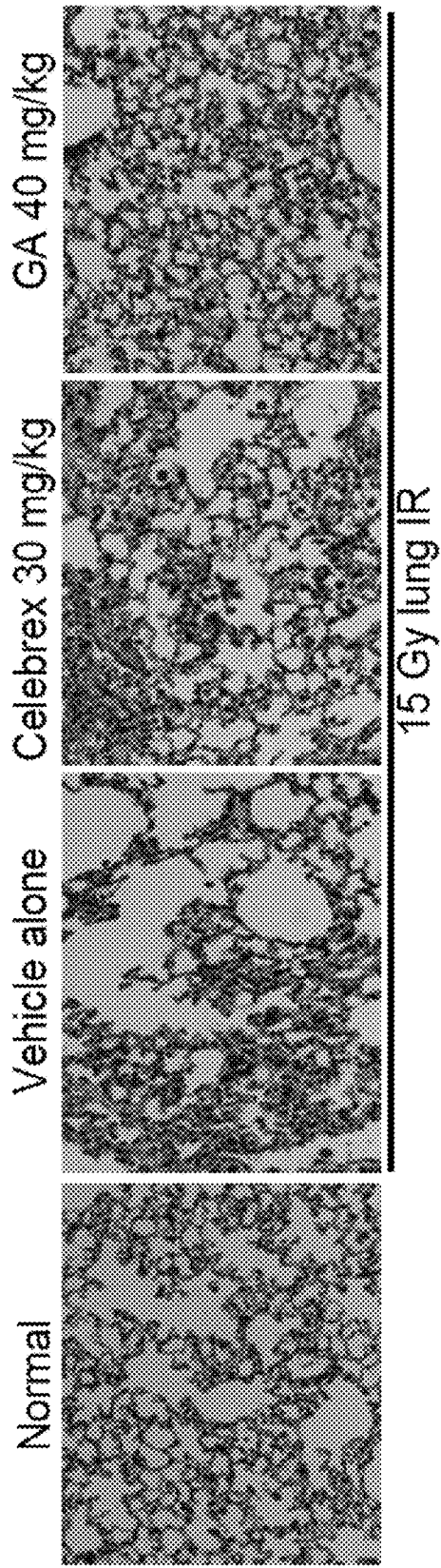
Fig 16  GA reduces IR-induced lung fibrosis
H&E staining at 7.5 months after 15 Gy lung IR ± GA, p.o. qod for 3 months

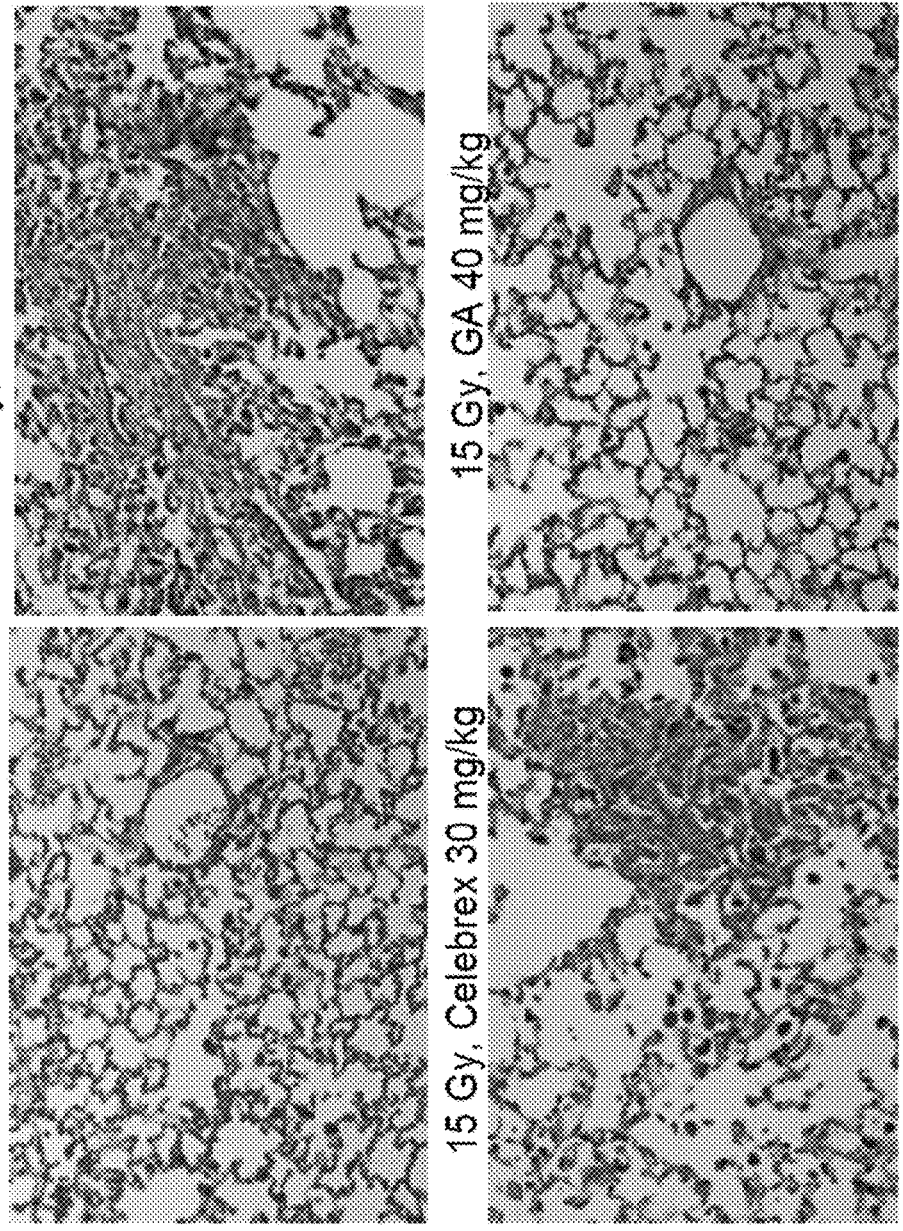

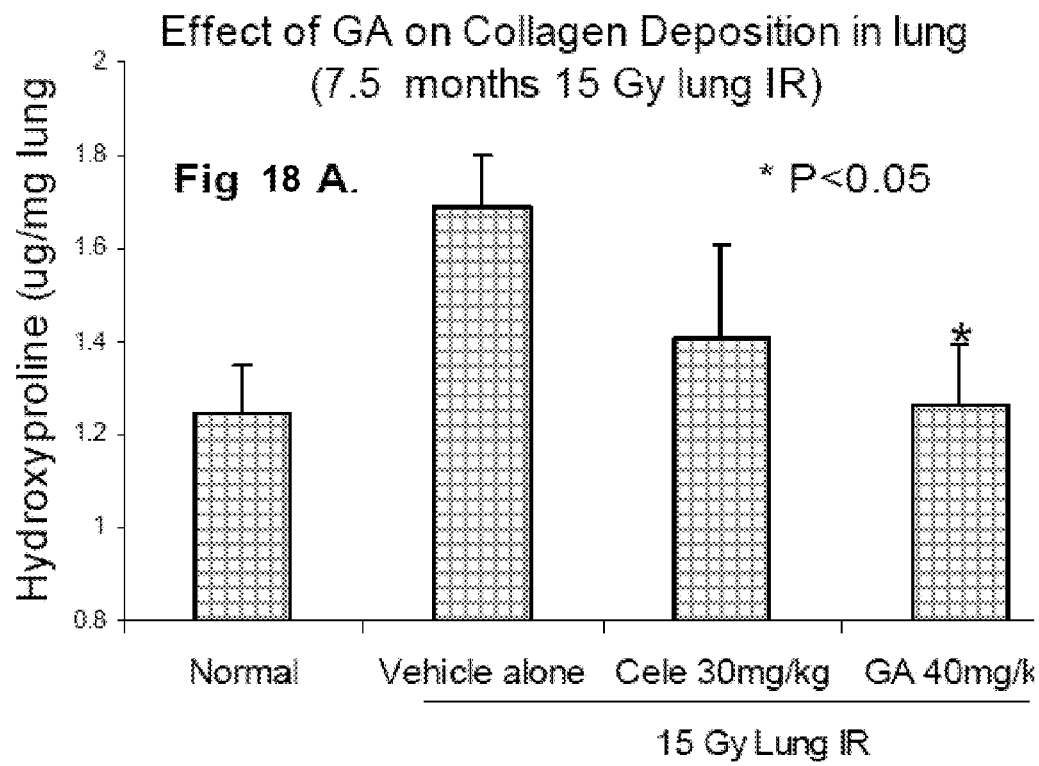
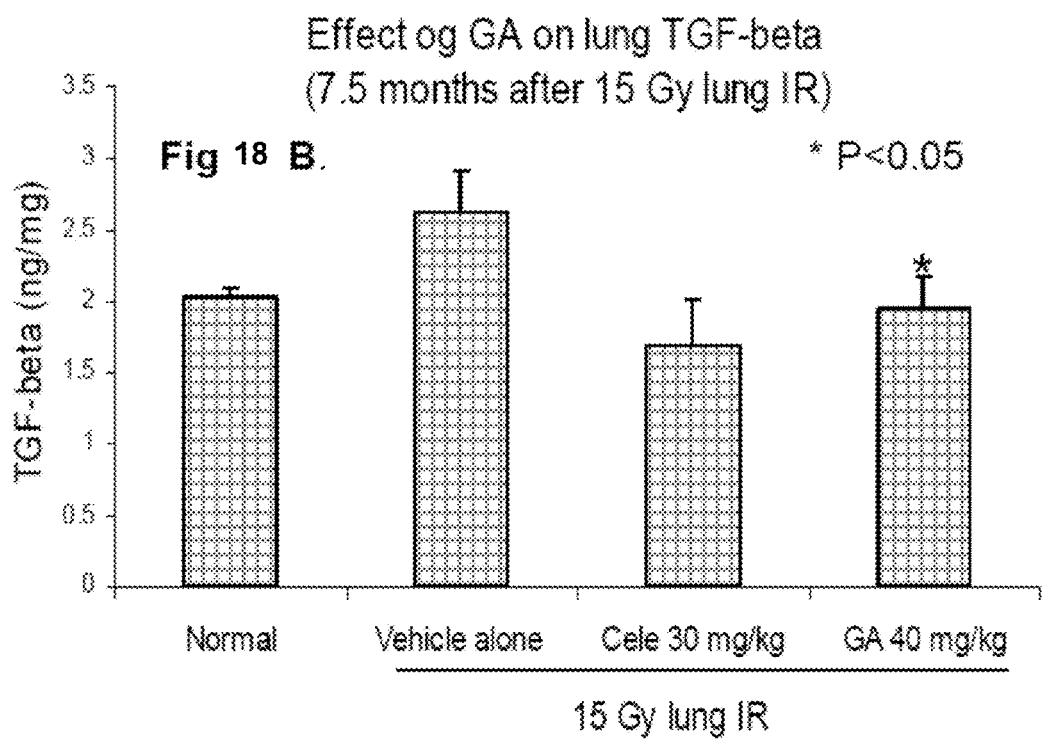

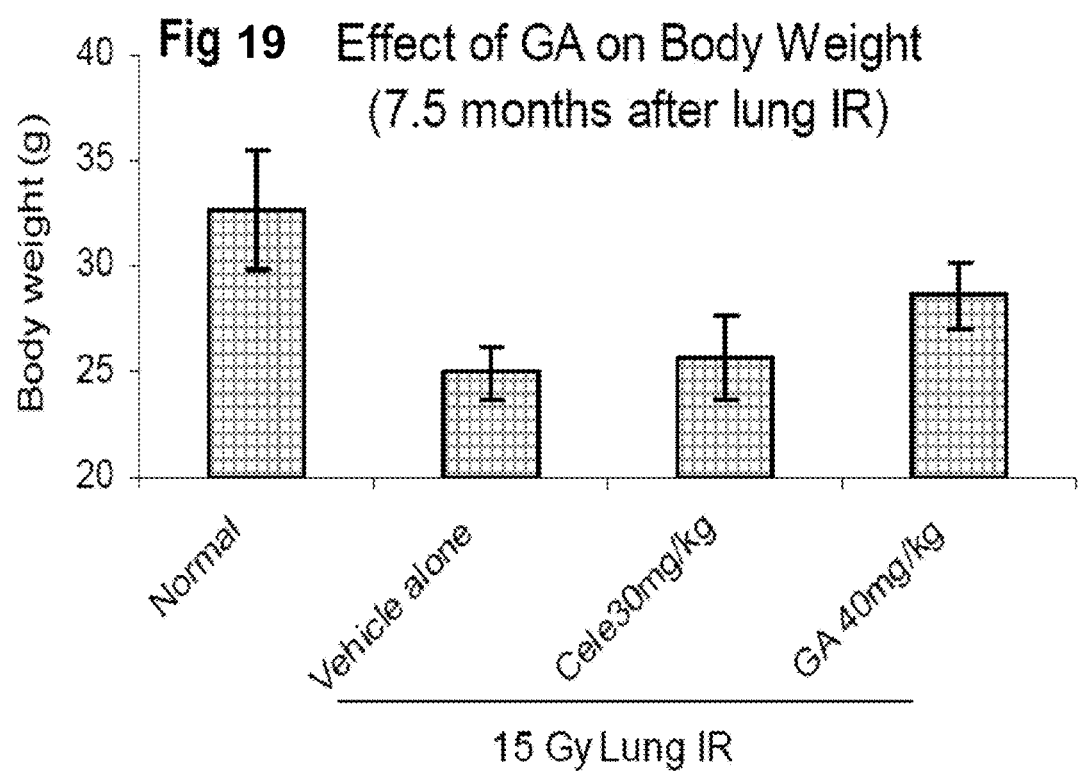

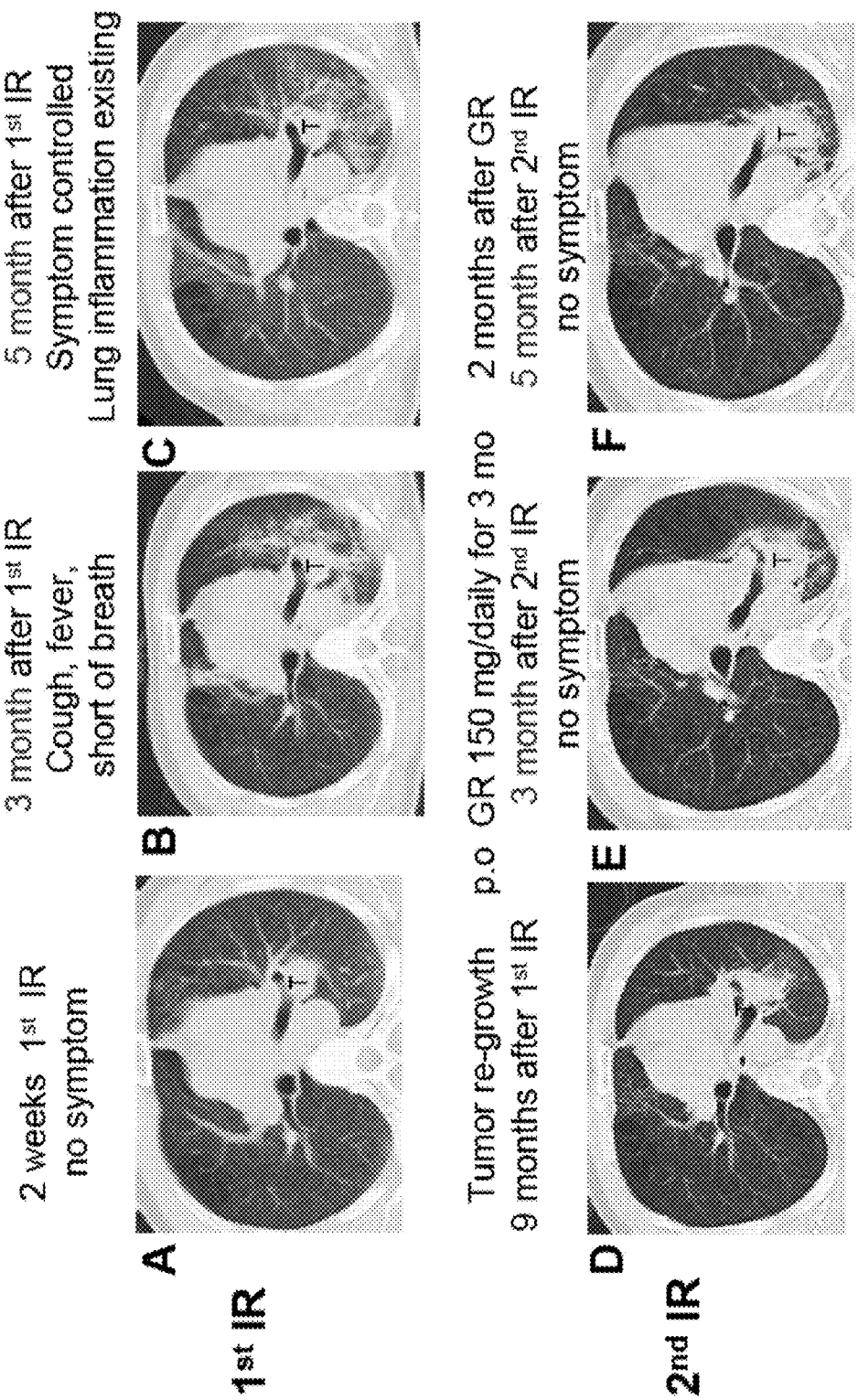

USE OF GLYCYRRHETINIC ACID, GLYCYRRHIZIC ACID AND RELATED COMPOUNDS FOR PREVENTION AND/OR TREATMENT OF PULMONARY FIBROSIS

TECHNICAL FIELD

The invention relates generally to uses of glycyrrhetinic acid, glycyrrhizic acid and related compounds for prevention and/or treatment of pulmonary fibrosis and lung diseases associated with pulmonary fibrosis.

BACKGROUND OF THE INVENTION

Pulmonary fibrosis (PF) is an insidious fibroproliferative condition characterized by a gradual replacement of normal parenchyma cells with fibrous, connective, matrix macromolecules (e.g., collagens, fibronectins and proteoglycans) on and within the lungs, usually at sites of injury or infection. The excessive formation of fibrous tissue, resulting from the activation and proliferation of fibroblast cells, destructs normal lung structure and function. For instance, the accumulation of fibrous tissue thickens alveolar walls, obliterates air space, and causes epithelial injury or even alveolar collapse. As a result, patients suffering from pulmonary fibrosis experience a varying degree of exertional dyspnea, and in late stages, orthopnea, cyanosis, and respiratory failure[1]. Median survival of pulmonary fibrosis is about 2-3 years and approximately 65% of patients die within 5 years of diagnosis.

Irradiation (IR) therapy, the most common treatment regime for tumor or cancer, may cause lung injury and ultimately lead to IR-induced pneumopathy including pulmonary fibrosis[1]. Risk of IR-induced pneumopathy further increases with concurrent administration of cytotoxic chemotherapeutic agents. IR-induced pneumopathy not only causes devastating effects on the quality of patient life, but sometimes can be even more life-threatening than the primary tumor or cancer[1]. Consequently, the risk of IR-induced pneumopathy, such as pulmonary fibrosis, has become a major dose-limiting factor and sometimes even prevents the use of irradiation therapy.

Currently, there is no cure for pulmonary fibrosis. While anti-inflammatory or pulmonary protective agents may alleviate symptoms of pulmonary fibrosis or improve patient life, they cannot halt disease progression. Common drugs for pulmonary fibrosis include amifostine, celebrex, and dexamethasone. While amifostine achieves certain cytoprotective effects against IR-induced pulmonary injury[2], it must be administered to patients 30 minutes prior to lung injury, and thus, cannot prevent or treat accidental lung injury. Celebrex, a widely used anti-inflammatory agent, has not been reported as effective for treatment of pneumonitis or pulmonary fibrosis. Dexamethasone is an anti-inflammatory steroid drug, and can cause serious side effects during long-term use. Further, the present inventors have observed that dexamethasone may result in worsening of pulmonary fibrosis, leading to lung failure or even earlier death as compared to the non-treated controls. Therefore, therapeutic agents with improved efficacy and safety are urgently needed. Traditional Chinese medicine has been practiced by the Chinese people for 2-3 millennia.

It deals with pathology, and diagnosis, treatment and prevention of diseases. Chinese medicinal materials have been recorded in various pharmacopoeia. One of the classical references for medicinal herbs is *Ben Cao Gang Mu* written by Li, Shizhen in the late 14$^{th}$ Century. The book contains about 2,500 items of herbs and other products including animals and minerals.

Liquorice (*Glycyrrhiza glabra*) has a long and diverse history of medicinal use in East Asian countries. Its root has been used as therapeutics for dermatitis and peptic ulcers. Glycyrrhizic acid (also known as Glycyrrhizin) (GLA) is a naturally-occurring compound that can be isolated from root of *Glycyrrhiza* species including Liquorice (*Glycyrrhiza glabra*). GLA is widely used as a flavoring agent in the United States and Europe, and has been approved by the State Food and Drug Administration of China for the treatment of chronic hepatitis and cirrhosis. Glycyrrhetinic acid (GA), a pentacyclic triterpenoid derivative that forms the functional motif of glycyrrhizic acid (GLA), has been used for the treatment of inflammation, peptic ulcer and infection. GA, GLA and related compounds, however, have not previously been reported to play any role in the treatment of pulmonary fibrosis.

BRIEF SUMMARY OF THE INVENTION

The present invention pertains to novel uses of glycyrrhetinic acid (GA), glycyrrhizic acid (GLA) and related compounds for prevention and/or treatment of pulmonary fibrosis and lung diseases associated with pulmonary fibrosis. The method comprises administering, to a subject in need of such treatment, an effective amount of one or more of the compounds and compositions of the present invention. Also described are therapeutic uses of prodrugs, metabolites, derivatives (e.g., acids, esters, ethers and amides), and salts of glycyrrhetinic acid (GA) and glycyrrhizic acid (GLA).

In one embodiment, the compounds and pharmaceutical compositions of the present invention can be used to treat or ameliorate pulmonary fibrosis including, but not limited to, radiation-induced pulmonary fibrosis and idiopathic pulmonary fibrosis.

The present invention also provides for therapeutic or pharmaceutical compositions comprising a compound of the invention in a form that can be combined with a pharmaceutically acceptable carrier. In preferred embodiments, the compositions are prepared in a form adapted for delivery into the lungs. The present invention also embodies nutritional supplements and health food or drink formulations comprising a compound of the invention.

BRIEF DESCRIPTION OF THE DRAWINGS

FIG. 10 shows that GA decreases respiratory rate of mice with IR-induced pulmonary fibrosis. (A) shows the reduction of respiratory rate 7 months after IR exposure at 15 Gy. (B) shows the reduction of respiratory rate 5 months after IR exposure at 18 Gy.

FIG. 14 show that GA reduces lung density in mice with IR-induced pulmonary fibrosis 7.5 months after IR exposure at 15 Gy.

FIG. 15 shows effects of GA on lung compliance 6.5 months after IR exposure at 15 Gy.

FIG. 16 shows that GA mitigates IR-induced pulmonary fibrosis.

FIG. 17 shows that GA mitigates IR-induced lung fibrosis.

FIG. 18 shows that GA reduces collagen deposition in mice with IR-induced pulmonary fibrosis.

FIG. 19 shows that GA increases the body weight of mice with IR-induced pulmonary fibrosis.

FIG. 20 shows that glycyrrhizic acid (GLA) mitigates pneumonitis in a cancer patient who received irradiation therapy.

DETAILED DISCLOSURE OF THE INVENTION

Figure 1A:
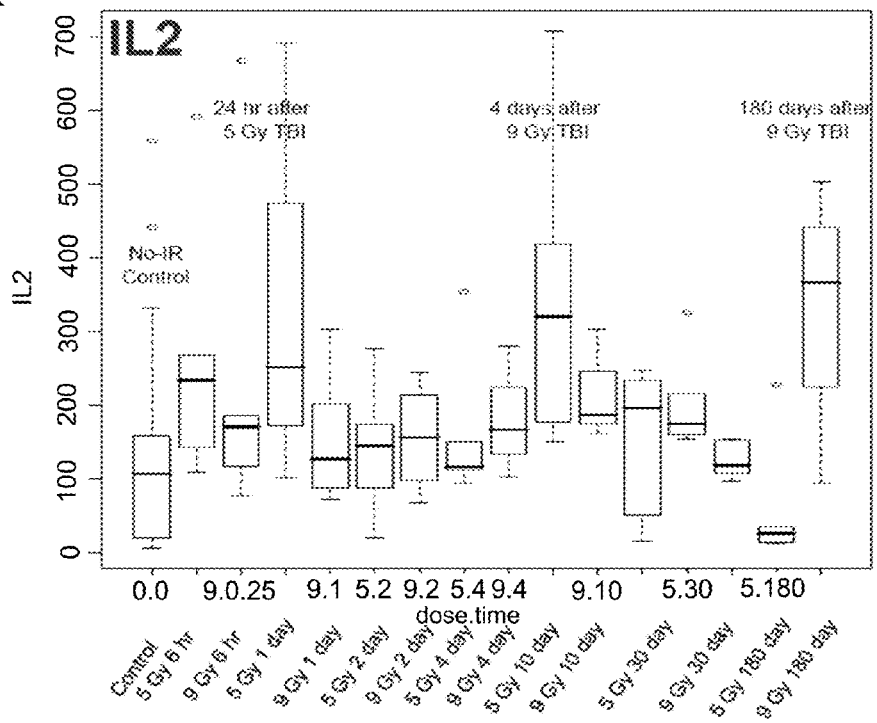
FIG. 1 shows induction of inflammatory responses by irradiation. (A)-(E) depict alternation of levels of inflammatory mediators (IMs) in mice exposed to IR at 0, 5, or 9 Gy.
Figure 1B:
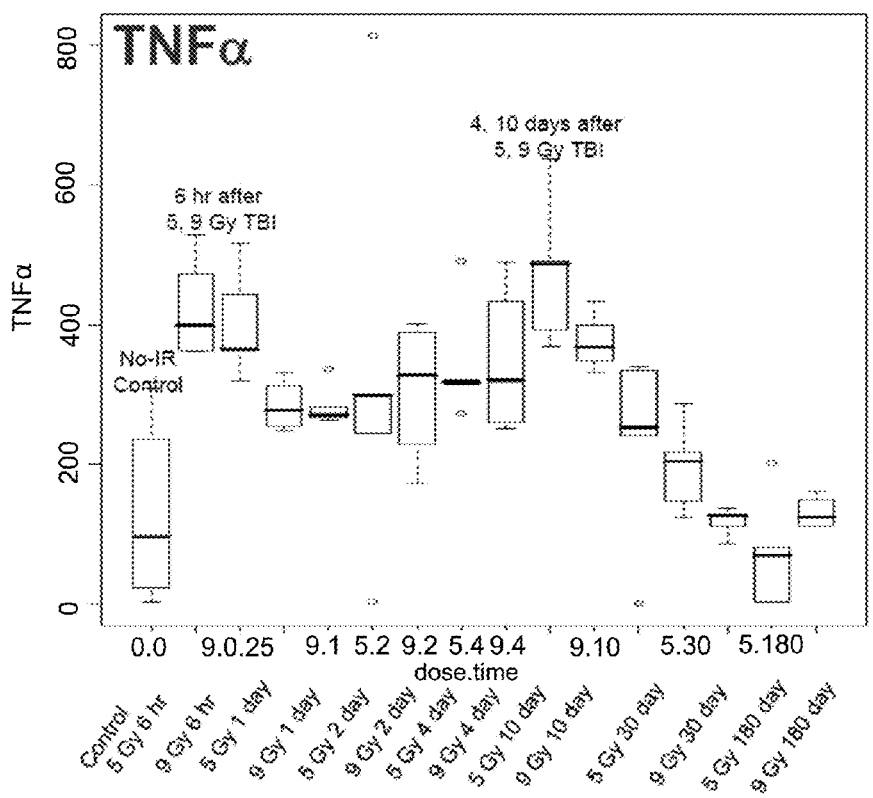
Figure 1C:
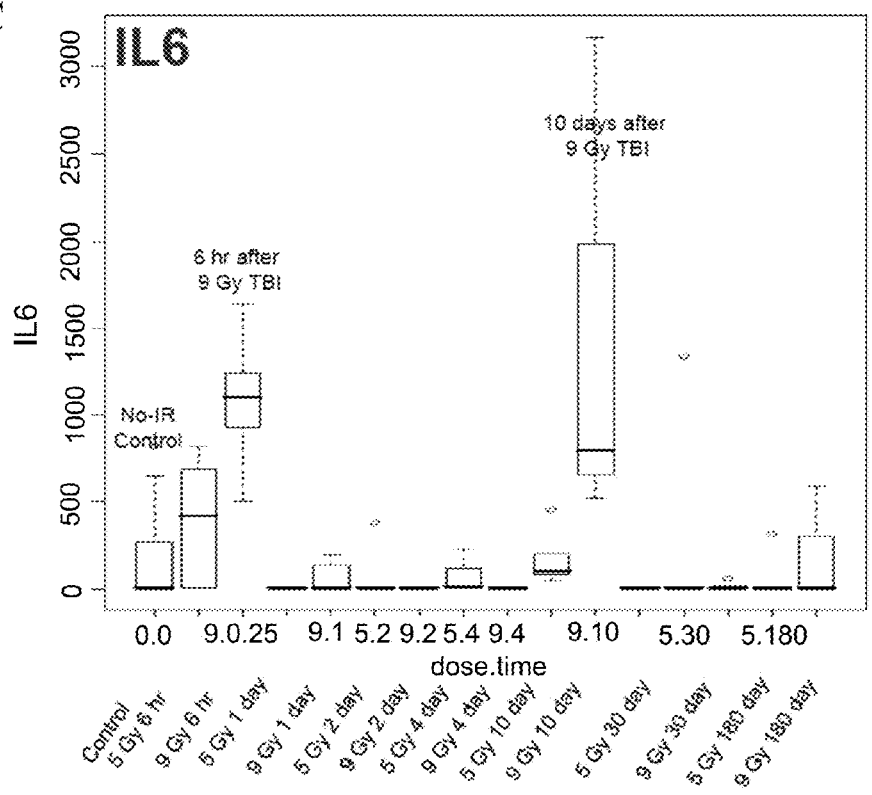
Figure 1D:
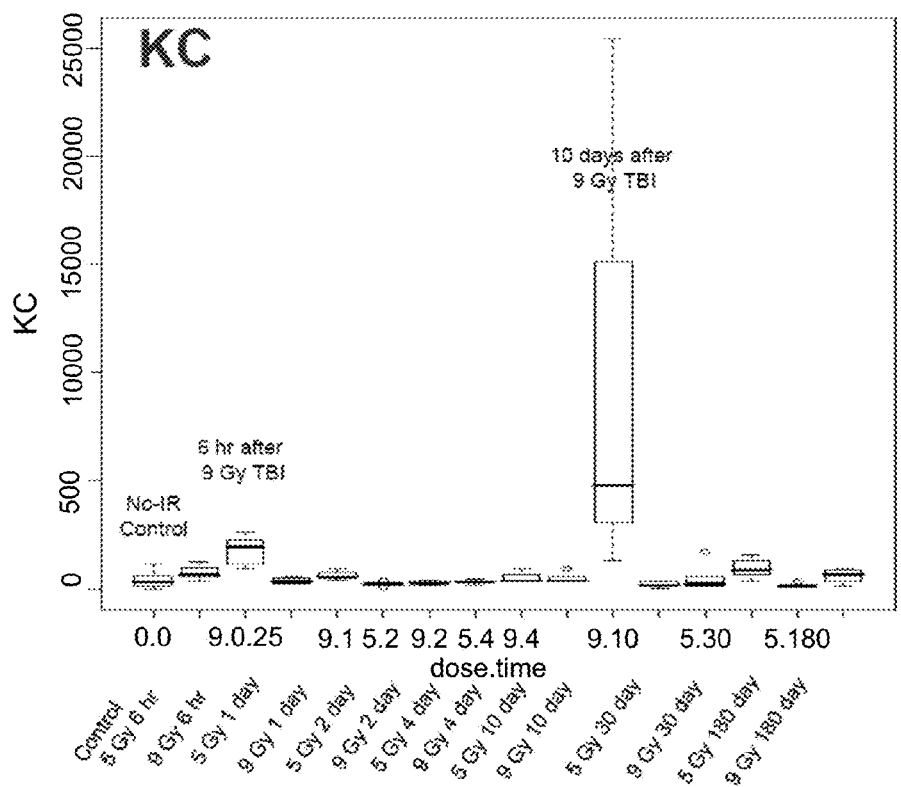
Figure 1E:
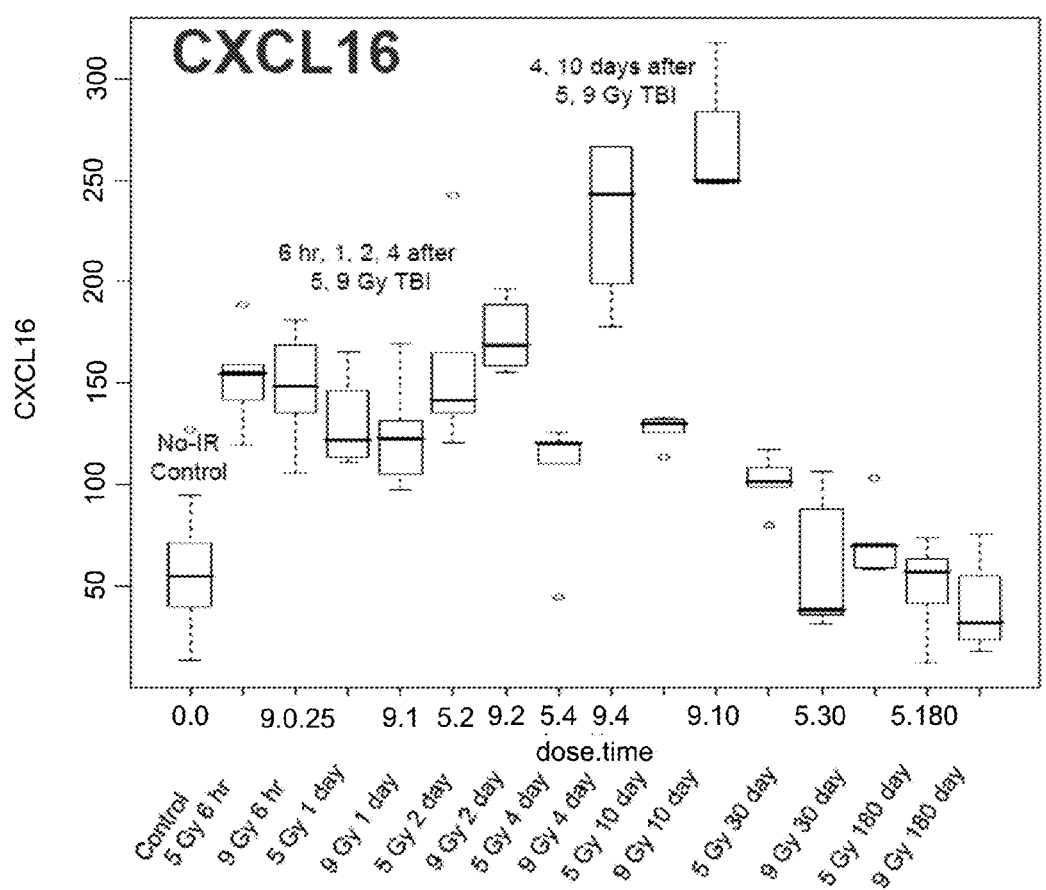
Figure 2D:
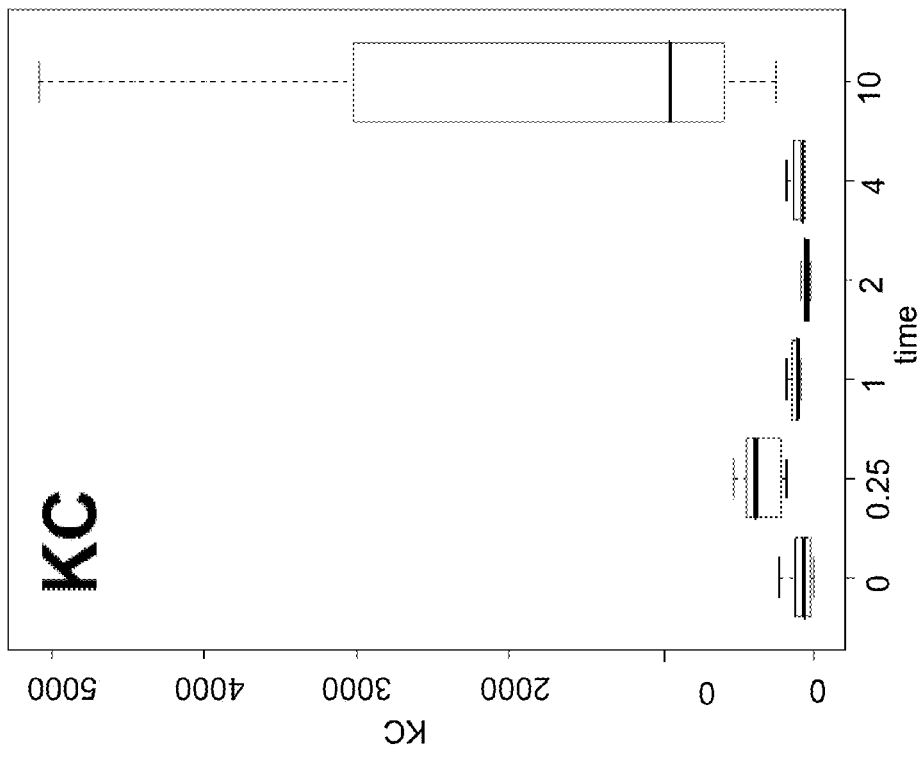
FIG. 2 shows the surge in IM levels in C57BL/6 and C3H/NeH mice with IR-induced brain injury (6 hr and 1, 2, 4 and 10 days after IR exposure at 9 Gy).
Figure 2C:
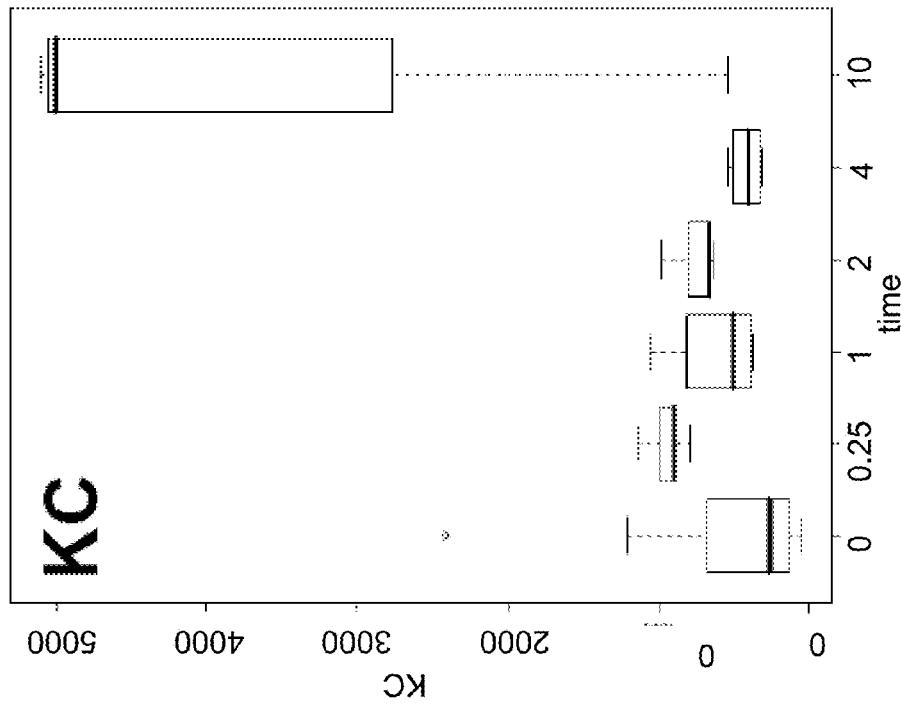
Figure 2F:
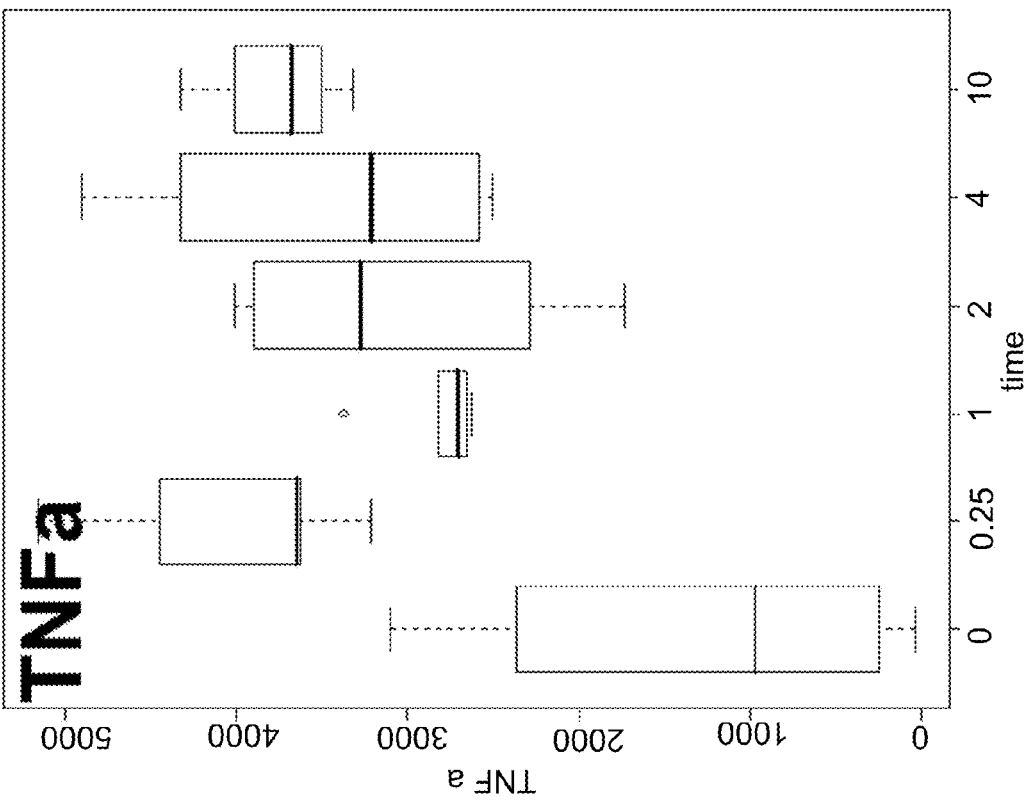
Figure 2E:
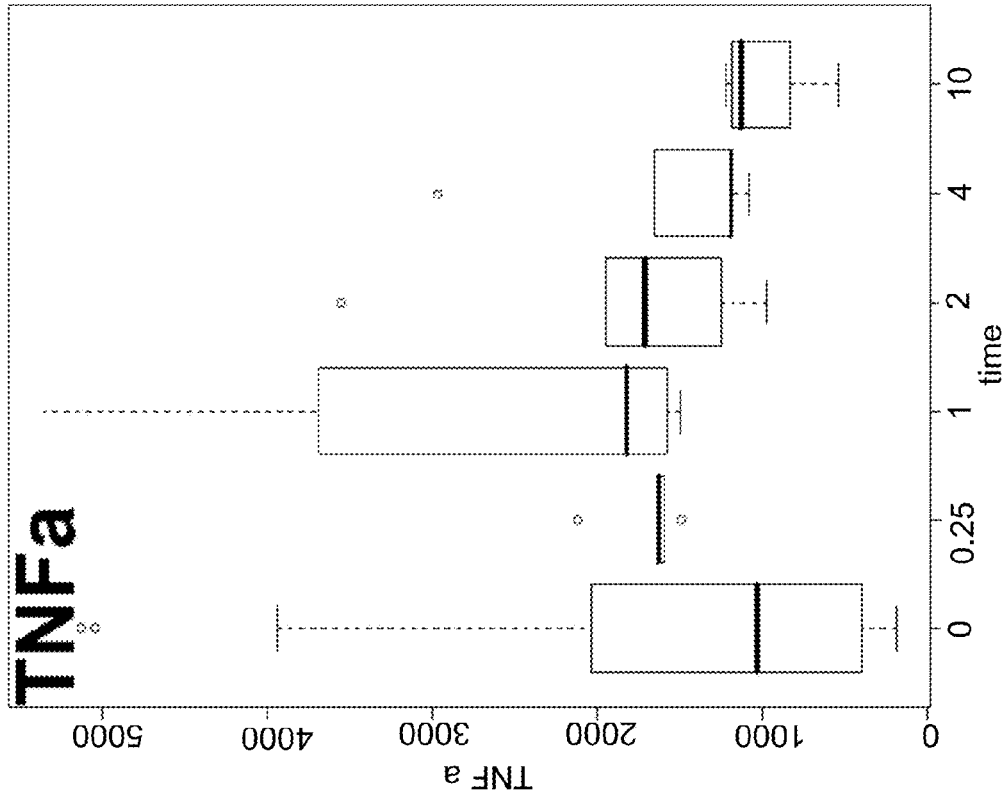
Figure 2H:
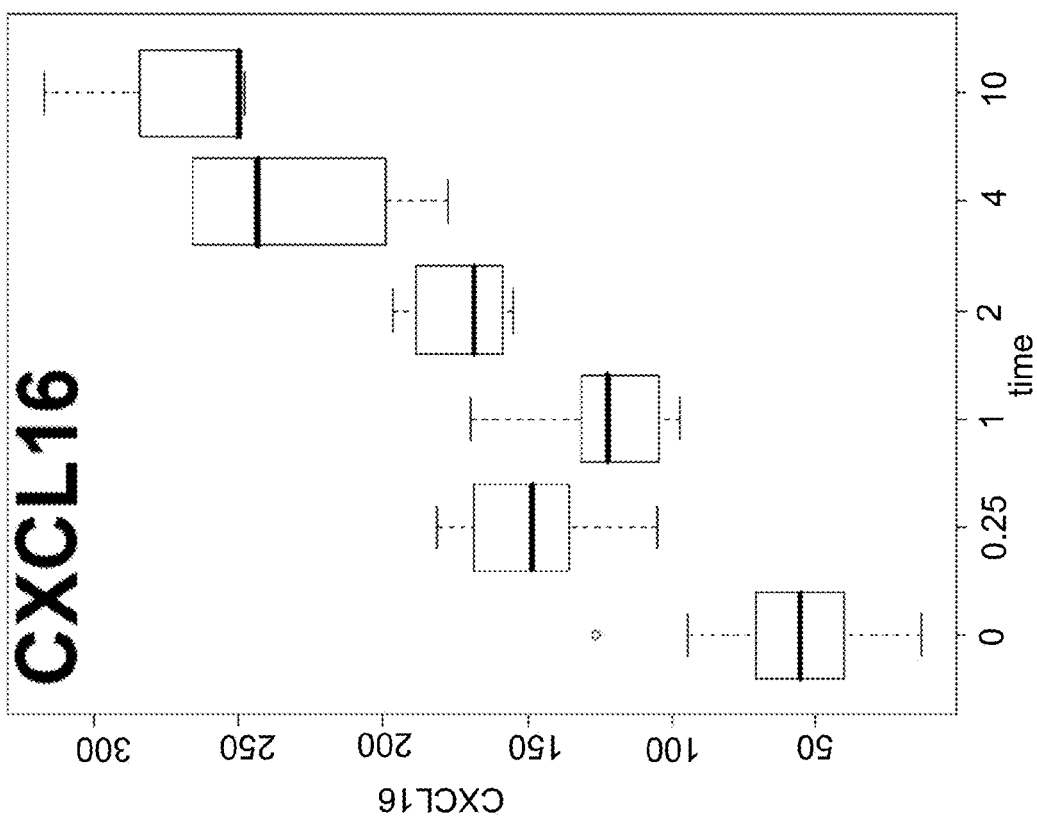
Figure 2G:
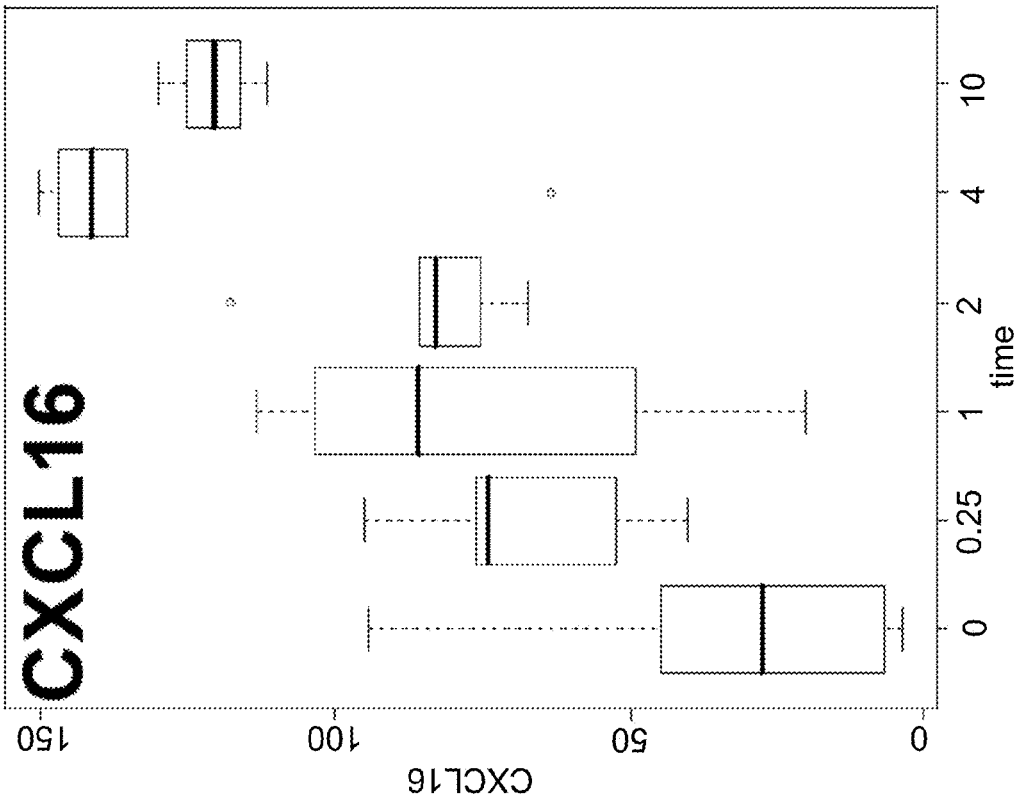
Figure 3A:
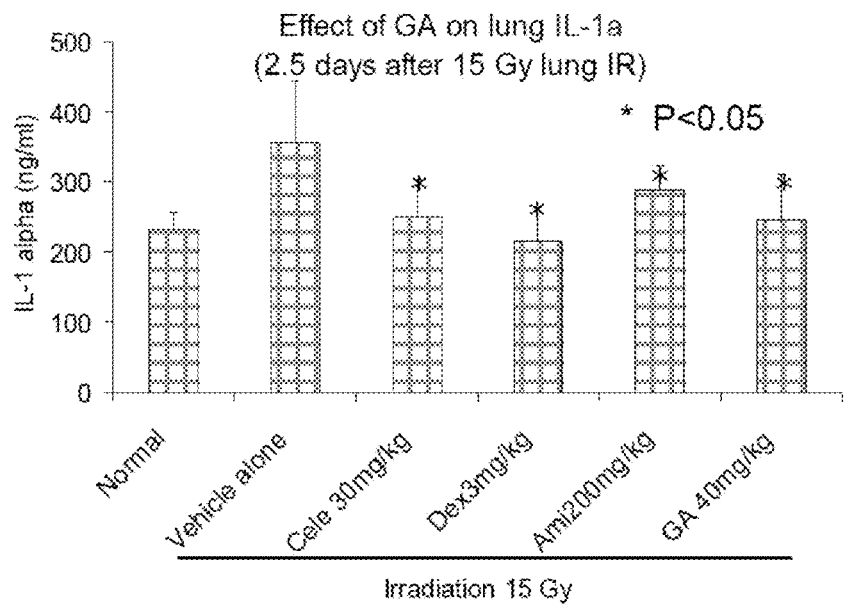
FIG. 3 shows inhibition effects of glycyrrhetinic acid (GA) on irradiation(IR)-induced inflammation during the acute phase of IR-induced pneumonitis.
Figure 3B:
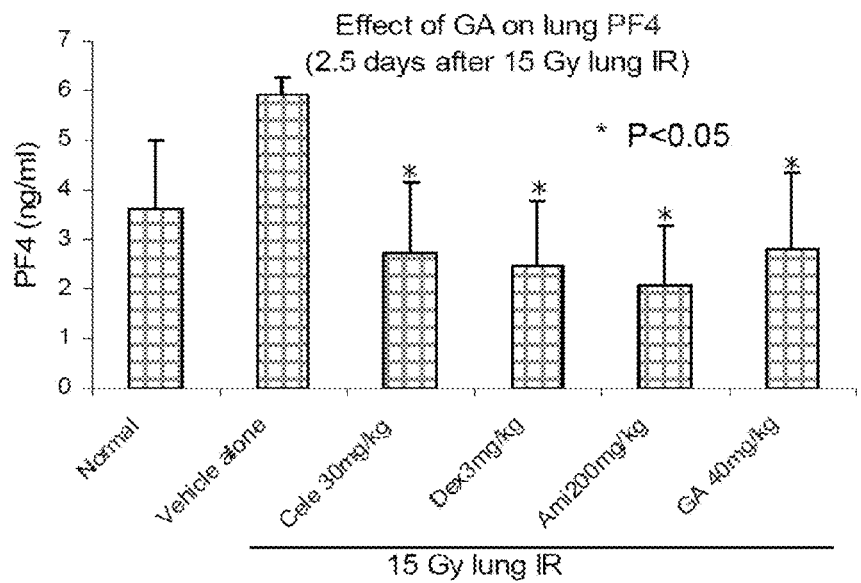
Figure 3C:
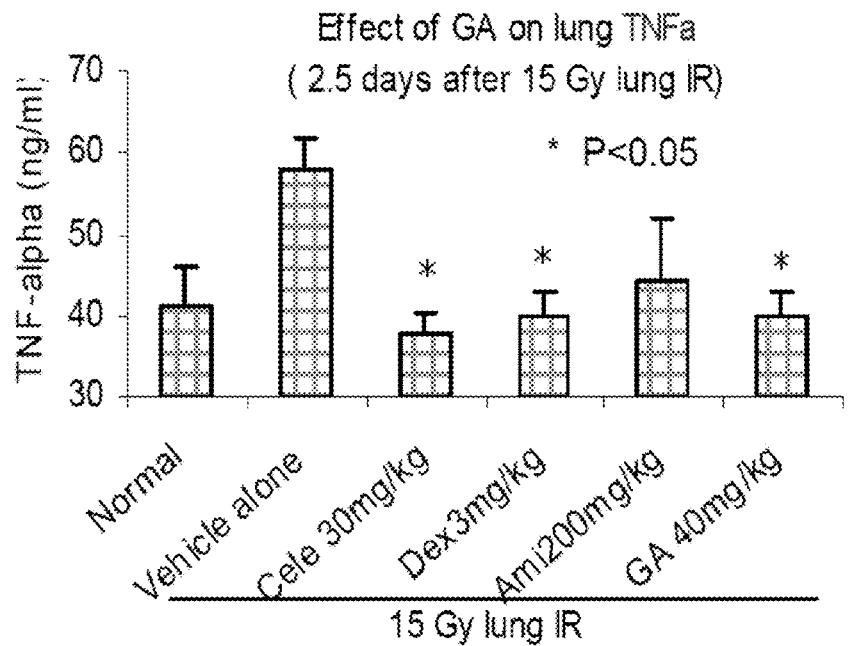
Figure 3D:
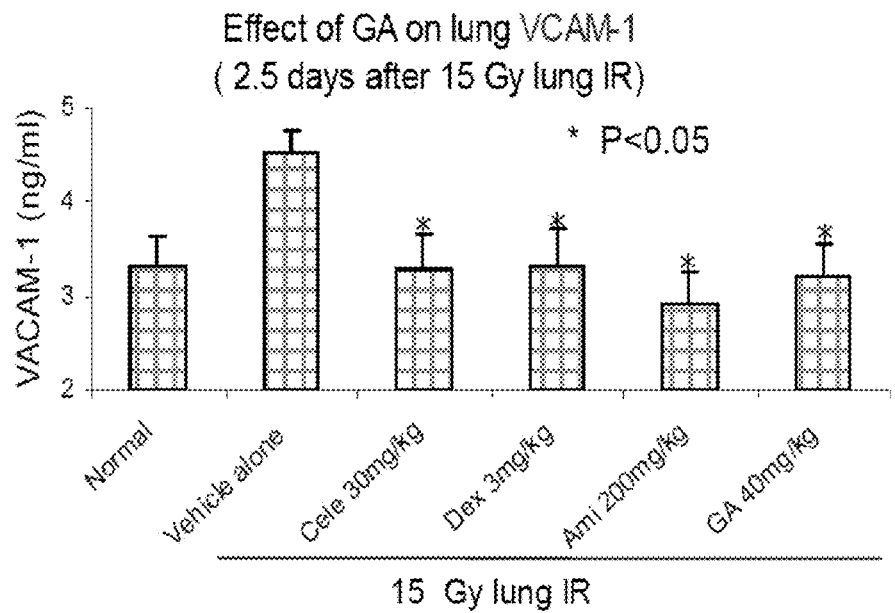

The present invention pertains to novel uses of glycyrrhetinic acid (GA), glycyrrhizic acid (GLA), and related compounds for the prevention and/or treatment of pulmonary fibrosis, in particular, irradiation-induced pulmonary fibrosis. Also described are therapeutic uses of prodrugs, metabolites, derivatives (e.g., acids, esters and ethers), and salts of glycyrrhetinic acid (GA) and glycyrrhizic acid (GLA).

In one embodiment, the method comprises administering, to a subject in need of such treatment, an effective amount of the compounds and compositions of the present invention. The present invention can also be used to treat lung diseases associated with pulmonary fibrosis.

The present invention also provides for therapeutic or pharmaceutical compositions comprising a compound of the invention in a form that can be combined with a pharmaceutically acceptable carrier. In preferred embodiments, the compositions are prepared in a form adapted for delivery into the lungs.

Compounds

The present invention pertains to therapeutic uses of glycyrrhetinic acid (GA), glycyrrhizic acid (GLA) and related compounds. Also described are therapeutic uses of prodrugs, metabolites, derivatives (e.g., acids, esters and ethers), and salts of glycyrrhetinic acid (GA) and glycyrrhizic acid (GLA).

It has now been discovered that GA and GLA effectively suppress lung inflammation, alleviate pulmonary injury, improve lung function, and reverse progressive deposition of fibrous tissues in lungs. Specifically, GA attenuates pulmonary inflammatory responses and significantly reduces levels of pulmonary-specific inflammatory mediators (e.g., IL-1, PF-4, SP-D, IL1a, TNFa, lymphotactin, p-selectin, 1-selectin, sTNF-R1, and VACAM-1) during the acute and sub-acute phases of pneumonitis. In addition, GA preserves the integrity of the alveolar-capillary barrier, as evidenced by the reduction of plasma exudation and inflammatory cell infiltration in GA-treated subjects. Further, GA significantly alleviates symptoms of pulmonary fibrosis, improves lung tissue morphology, and suppresses excessive collagen deposition in lungs.

In one embodiment, the present invention pertains to glycyrrhetinic acid (GA) (MW:470.68), having the following structure (Structure A):

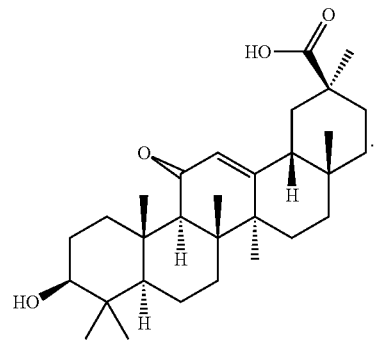

In another embodiment, the present invention pertains to glycyrrhizic acid (GLA) (MW:822.93), a triterpenoid saponin glycoside of glycyrrhetinic acid, having the following structure (Structure B):

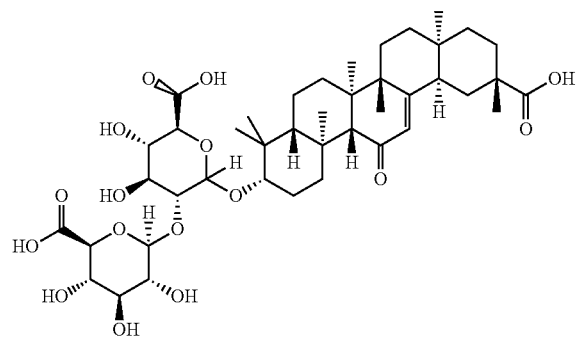

Glycyrrhizic acid can be isolated from the root of liquorice (*Glycyrrhiza glabra*) or other Glycyrrhiza species.

In certain embodiments, the present invention pertains to ester, ether and/or amide forms of glycyrrhetinic acid (GA), represented by the following structure (Structure C):

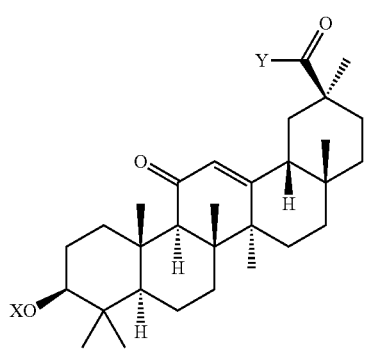

wherein

X represents any group that forms an ether or ester bond with the hydroxy radical; and Y represents any group that forms an ester or amide bond with the carboxy group.

In certain embodiments, the present invention pertains to ester and/or amide forms of glycyrrhizic acid (GLA), represented by the following structure (Structure D):

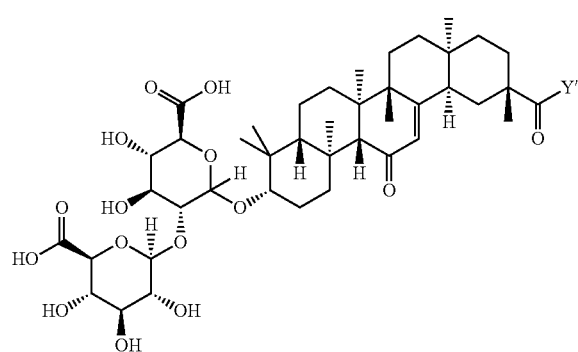

wherein Y' represents any group that forms an ester or amide bond with the carboxy group.

In certain embodiments, X can be alkyl, substituted alkyl (e.g., haloalkyl and hydroxyalkyl), alkenyl, substituted alkenyl, —COOH, acyl, alkylcarbonyl, benzyl, cyclic alkyl, or cyclic alkenyl.

In certain embodiments, X can be an organic or inorganic acid group including, but not limited to, acetic acid, carboxylic acid, aspartic acid, formic acid, citric acid, benzoic acid, hippuric acid, malic acid, mucic acid, phosphoric acid, sulfuric acid, gluconic acid, maleic acid, succinic acid, tartaric, and lactic acid.

In certain embodiments, X can be a carbohydrate moiety, in which a monosaccharide, disaccharide, oligosaccharide, or its derivative loses an —H in its hydroxyl group and thereby forms a radical. Suitable carbohydrate moieties can be derived, for example, from glucose, fructose, and sucrose.

In certain embodiments, Y and Y' can be —NH$_2$, alkylamino, or alkoxy.

"Alkyl" means a linear saturated monovalent radical of one to sixteen carbon atoms or a branched saturated monovalent of three to sixteen carbon atoms. It may include hydrocarbon radicals of one to four or one to three carbon atoms, which may be linear. Examples include methyl, ethyl, propyl, 2-propyl, n-butyl, iso-butyl, tert-butyl, pentyl, and the like.

"Alkenyl" means a linear or branched $C_2$-$C_{16}$ hydrocarbon radical that comprises one or more carbon-carbon double bonds. Examples include propylenyl, buten-1-yl, isobutenyl, penten-1-yl, 2,2-methylbuten-1-yl, 3-methylbuten-1-yl, hexan-1-yl, hepten-1-yl, octen-1-yl, and the like.

"Acyl" means a radical —C(O)R where R is hydrogen, alkyl or cycloalkyl, or heterocycloalkyl.

Examples include formyl, acetyl, ethylcarbonyl, and the like.

"Carboxyl" means the radical —C(O)OH.

"Carboalkoxy" means a radical —C(O)R where R is, for example, hydrogen, alkyl or cycloalkyl, heterocycloalkyl, halo, or alkyl halo.

"Halo" means fluoro, chloro, bromo fluoro, chloro, bromo, or iodo, such as bromo and chloro.

"Haloalkyl" means alkyl substituted with one or more same or different halo atoms, e.g., —CH$_2$Cl, —CH$_2$Br, —CF$_3$, —CH$_2$CH$_2$Cl, —CH$_2$CCl$_3$, and the like.

"Amino" means the radical —NH$_2$.

"Alkylamino" means a radical —NHR or —NR$_2$ where each R is independently an alkyl group. Examples include methylamino, (1-methylethyl)amino, dimethyl amino, methylethylamino, di(1-methyethyl)amino, and the like.

"Hydroxy" means the radical —OH.

"Hydroxyalkyl" means an alkyl radical as defined herein, substituted with one or more, preferably one, two or three hydroxy groups. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4- hydroxybutyl, 2,3-dihydroxypropyl, 2-hydroxy-1- hydroxymethyl ethyl, 2,3-dihydroxybutyl, 3,4-dihydroxybutyl and 2-(hydroxymethyl)-3-hydroxy-propyl, preferably 2-hydroxyethyl, 2,3-dihydroxypropyl and 1-(hydroxymethyl) 2-hydroxyethyl.

"Alkoxy" means the radical —OR$_a$, where R$_a$ is an alkyl group or substituted alkyl group.

Exemplary alkoxy groups include methoxy, ethoxy, propoxy, and the like.

In one embodiment, the present invention pertains to acetoxolone ($C_{32}H_{48}O_5$, CAS No. 6277-14-1), an acetyl derivative of glycyrrhizic acid.

The present invention also pertains to salt forms of GA, GLA and related compounds including, but not limited to, ammonium salts, sodium salts, and potassium salts.

The present invention also pertains to uses of prodrugs and metabolites of the compounds. The term "prodrug," as used herein, refers to a metabolic precursor of a compound of the present invention or pharmaceutically acceptable form thereof. In general, a prodrug comprises a functional derivative of a compound, which may be inactive when administered to a subject, but is readily convertible in vivo into an active metabolite compound.

Conventional procedures for the selection and preparation of suitable prodrug derivatives are described, for example, in "Design of Prodrugs", ed. H. Bundgaard, Elsevier, 1985. Preferably, a prodrug of the present invention enhances desirable qualities of the compound of the present invention including, but not limited to, solubility, bioavailability, and stability. Hence, the compounds employed in the present methods may, if desired, be delivered in a prodrug form. Prodrugs of the compounds employed in the present invention may be prepared by modifying functional groups present in the compound such that the modifications are cleaved, either in routine manipulation or in vivo, to the parent compound.

The term "metabolite," refers to a pharmacologically active product, including for example, an active intermediate or an ultimate product, produced through in vivo metabolism of a compound of the present invention in a subject. A metabolite may result, for example, from the anabolic and/or catabolic processes of the administered compound in a subject, including but not limited to, the oxidation, reduction, hydrolysis, amidation, deamidation, esterification, deesterification, enzymatic cleavage, and the like.

Metabolites are typically identified by preparing a radiolabelled (e.g., $^{14}C$ or $^{3}H$) isotope of a compound of the present invention, administering it parenterally in a detectable dose (e.g., greater than about 0.5 mg/kg) to an animal such as rat, mouse, guinea pig, monkey, or to a human, allowing sufficient time for metabolism to occur (typically about 30 seconds to about 30 hours), and isolating its conversion products from the urine, blood or other biological samples. These products are easily isolated since they are labeled (others are isolated by the use of antibodies capable of binding epitopes surviving in the metabolite). The structure of metabolites can be determined in conventional fashion, e.g., by MS, LC/MS or NMR analysis. In general, analysis of metabolites is performed according to techniques well known to those skilled in the art of drug metabolism studies.

The present invention further pertains to isolated enantiomeric compounds. The isolated enantiomeric forms of the compounds of the invention are substantially free from one another (i.e., in enantiomeric excess). In other words, the "R" forms of the compounds are substantially free from the "S" forms of the compounds and are, thus, in enantiomeric excess of the "S" forms. Conversely, "S" forms of the compounds are substantially free of "R" forms of the compounds and are, thus, in enantiomeric excess of the "R" forms. In one embodiment of the invention, the isolated enantiomeric compounds are at least about in 80% enantiomeric excess. In a preferred embodiment, the compounds are in at least about 90% enantiomeric excess. In a more preferred embodiment, the compounds are in at least about 95% enantiomeric excess. In an even more preferred embodiment, the compounds are in at least about 97.5% enantiomeric excess. In a most preferred embodiment, the compounds are in at least about 99% enantiomeric excess.

In an embodiment, the compounds of the present invention have the same chiral structure as shown in any of Structures A-D.

Prevention and/or Treatment of Pulmonary Fibrosis

The present invention provides methods for prevention and/or treatment of pulmonary fibrosis, in particular, irradiation-induced pulmonary fibrosis. The present methods can also be used to prevent, treat or ameliorate lung diseases associated with pulmonary fibrosis.

In one embodiment, the method comprises administering, to a subject in need of such treatment, an effective amount of the compounds and compositions of the present invention. Preferably, the compounds and compositions of the present invention are prepared in a form for administration to the lungs.

The term "pulmonary fibrosis" or "lung fibrosis", as used herein, refers to abnormal formation or accumulation of fibrous, connective, or scar tissues and/or matrix macromolecules (e.g., collagens, fibronectins, proteoglycans) on and/or within lungs. Symptoms of pulmonary fibrosis include shortness of breath, dry cough, increased respiratory rate, decreased lung compliance, increased lung density, chest discomfort, and rapid weight loss. Pulmonary fibrosis does not encompass any fibrotic condition that develops in organs other than lungs, such as fibrotic conditions that develop in the liver.

The term "treatment" or any grammatical variation thereof (e.g., treat, treating, and treatment etc.), as used herein, includes but is not limited to, ameliorating or alleviating a symptom of a disease or condition, reducing, suppressing, inhibiting, lessening, or affecting the progression, severity, and/or scope of a condition. In one embodiment, treatment refers to reducing, suppressing, inhibiting, lessening, or affecting the progression, severity, and/or scope of abnormal formation or accumulation of fibrous, connective, or scar tissues and/or matrix macromolecules (e.g., collagens, fibronectins and proteoglycans) on or within lungs.

The term "prevention" or any grammatical variation thereof (e.g., prevent, preventing, and prevention etc.), as used herein, includes but is not limited to, delaying the onset of symptoms, preventing relapse to a disease, increasing latency between symptomatic episodes, or a combination thereof. Prevention, as used herein, does not require the complete absence of symptoms.

Lung diseases associated with pulmonary fibrosis include complications of pulmonary fibrosis, lung diseases that would develop into pulmonary fibrosis, and lung diseases that arise from pulmonary fibrosis. Symptoms and complications of pulmonary diseases include, but are not limited to, hypoxemia, dyspnea, othopnea, cyanosis, pulmonary hypertension, cor pulmonale, and lung dysfunction. Lung conditions that could develop into pulmonary diseases include, but are not limited to, injury to lungs (e.g., irradiation, chemicals, medications, biological injury and pollutants), lung infection (e.g., viral, bacterial, fungal and parasitic infection), interstitial lung diseases, lung injury induced by parasitic infection, and pneumonitis.

"Pneumonitis," as used herein, refers to its ordinary meaning, which is inflammation of lung tissue.

The term "effective amount," as used herein, refers to an amount that is capable of preventing, ameliorating, or treating pulmonary fibrosis. For instance, an effective amount is an amount capable of alleviating one or more symptoms of pulmonary fibrosis. In certain embodiments, the effective amount enables at least 5%, 10%, 15%, 20%, 25%, 30%, 35%, 40%, 45%, 50%, 60%, 70%, 80%, 90%, or 100% decrease in respiratory rate, decrease in lung density, increase in body weight, and/or increase in lung compliance, as compared to non-treated subjects with pulmonary fibrosis.

In a specific embodiment, the effective amount enables at least 5%, 10%, 15%, 20%, 25%, 30%, 35%, 40%, 45%, 50%, 60%, 70%, 80%, 90%, or 100% reduction in abnormal accumulation of fibrous materials (e.g., collagens, fibronectins and proteoglycans) in lungs, as compared to non-treated subjects with pulmonary fibrosis. For instance, the effective amount enables at least 5%, 10%, 15%, 20%, 25%, 30%, 35%, 40%, 45%, 50%, 60%, 70%, 80%, 90%, or 100% reduction in collagen, fibronectin, proteoglycan and/or hydroxyproline content in lungs, as compared to non-treated subjects with pulmonary fibrosis. For another instance, the effective amount enables at least 5%, 10%, 15%, 20%, 25%, 30%, 35%, 40%, 45%, 50%, 60%, 70%, 80%, 90%, or 100% reduction in pro-fibrotic mediators such as TGFβ in lung tissue, as compared to non-treated subjects with pulmonary fibrosis.

Additionally, as pulmonary fibrosis arises, in many instances, from inflammatory responses to lung injury or infection, an effective amount is capable of reducing the levels of one or more pulmonary inflammatory mediators in lung tissue. Exemplified pulmonary inflammatory mediators include, but are not limited to, SP-D, IL1a, TNFa, IL6, PF4, P-selectin, L-selectin, VCAM-1, lymphotactin, and prostaglandin E (PGE). In certain embodiments, the effective amount enables at least 5%, 10%, 15%, 20%, 25%, 30%, 35%, 40%, 45%, 50%, 60%, 70%, 80%, 90%, or 100% reduction in the levels of one or more inflammatory mediators, as compared to non-treated subjects with pulmonary fibrosis.

The term "subject," as used herein, describes an organism, including mammals such as primates, to which treatment with the compositions according to the present invention can be provided. Mammalian species that can benefit from the disclosed methods of treatment include, but are not limited to, apes, chimpanzees, orangutans, humans, monkeys; and domesticated animals such as dogs, cats, horses, cattle, pigs, sheep, goats, chickens, mice, rats, guinea pigs, and hamsters.

"A subject in need of such treatment", as used herein, refers to a subject who is specifically at risk of, has symptoms of, or is diagnosed with, pulmonary fibrosis and/or lung diseases associated with pulmonary fibrosis. In a specific embodiment, the present invention comprises diagnosing whether a subject has pulmonary fibrosis, wherein the compounds and compositions of the present invention are administered to the subject who is diagnosed with, or has symptoms of, pulmonary fibrosis.

The identification of subjects who have pulmonary fibrosis is well within the knowledge and ability of one skilled in the art. By way of example, a clinician skilled in the art can readily, by the use of physical exams such as pulmonary function test and exercise test, identify observable symptoms of pulmonary fibrosis. In addition, a combination of medical techniques, such as chest X-day, high resolution computerized tomography (HRCT), and surgical lung biopsy, can be employed to determine the pathological alteration of lung tissues caused by pulmonary fibrosis.

In another embodiment, the compounds and compositions of the present invention are administered to a subject who has no observable symptoms of pulmonary fibrosis, but has been determined to be susceptible to developing pulmonary fibrosis (hereinafter such a patient is referred to as an "at-risk patient"). For instance, "at-risk patients" include subjects who had injury to the lung (e.g., irradiation, chemicals, medications, biological injury and pollutants), lung infection (e.g., viral, bacterial, fungal and parasitic infection), and diseases such as pneumonitis and interstitial lung diseases. In a specific embodiment, a patient is assessed to identify the risk of developing pulmonary fibrosis, prior to the administration of the compounds and compositions of the present invention. In a further specific embodiment, the subject is a cancer patient who received, or is receiving, irradiation therapy.

In an embodiment, the compounds and pharmaceutical compositions of the present invention can be used to prevent, treat or ameliorate pulmonary fibrosis including, but not limited to, radiation-induced pulmonary fibrosis, idiopathic pulmonary fibrosis, and cystic lung fibrosis.

In a specific embodiment, the present invention can be used to prevent, treat or ameliorate radiation-induced lung injury and/or radiation pneumopathy including pneumotitis and pulmonary fibrosis. In an embodiment, the present invention can be used to prevent, treat or ameliorate pulmonary fibrosis induced by irradiation therapy for tumor or cancer treatment. In another embodiment, the present invention can be used to prevent, treat or ameliorate pulmonary fibrosis induced by accidental lung injury caused by irradiation or nuclear incidents.

In a specific embodiment, the present invention can be used to prevent, treat or ameliorate pulmonary fibrosis induced by thoracic irradiation. In certain embodiments, the present invention can be used to prevent, treat or ameliorate pulmonary fibrosis induced by radiation at a dose of at least 1, 2, 3, 4, 5, 6, 7, 8, 9, 10, 15, 20, 25, 30, 35, 40, 45, 50, 55, 60, 65, 70, 80, 85, 90, 95, 100, 120, or 150 Gy. In addition, the present invention can be used to prevent, treat or ameliorate pulmonary fibrosis induced by radiation at a dose of at least 0.1, 0.3, 0.5, 0.7, 0.9, 1.0, 1.1, 1.2, 1.3, 1.4, 1.5, 1,6, 1.7, 1.8, 1.9, 2.0, 2.1, 2.2, 2.3, 2.4, 2.5, 2,7, 3.0, 3.2, 3.5, or 4.0 Gy per day.

In one embodiment, the compounds and pharmaceutical compositions of the present invention can be used to prevent, treat or ameliorate pulmonary fibrosis induced by irradiation (including irradiation therapy), pollutants, toxins, trauma, cigarette smoking, autoimmune diseases such as rheumatoid arthritis, medications (e.g., amiodarone, bleomycin, busulfan, methotrexate, and nitrofurantoin), asbestos, and infection (e.g. viral, bacterial, fungal and parasitic infection).

In one embodiment, the compounds and pharmaceutical compositions of the present invention can be used to prevent, treat or ameliorate disease that would develop into pulmonary fibrosis, including interstitial lung diseases, acute and/or chronic pneumonitis, chronic obstructive pulmonary disease (COPD), asthma, silicosis, lung injury, and pneumonia.

In one embodiment, the compounds and pharmaceutical compositions of the present invention can be used to prevent, treat or ameliorate fibrotic diseases or conditions that develop in skin, heart, intestine, and/or retroperitoneum. In an embodiment, the present invention excludes treatment of liver fibrosis.

While in the experimental models of the present invention pulmonary fibrosis was induced using thoracic irradiation, it would be readily understood that the therapeutic benefits of the present invention extend beyond. IR-induced pulmonary fibrosis.

In a further embodiment, the present invention does not encompass the treatment of inflammation of tissues other than lung tissues. In an embodiment, the present invention does not encompass the treatment of inflammatory conditions in the liver or skin. In another embodiment, the present invention does not encompass the treatment of one or more inflammatory conditions and diseases, including hepatitis, cirrhosis, hypertension, and non-pulmonary edema. In another embodiment, the present invention does not encompass the treatment of viral (e.g., Influenza A, HSV, SARS and/or HIV), bacterial (e.g., *Staphylococcus*), or fungal infection that does not develop into pulmonary fibrosis. In another embodiment, the present invention does not encompass the treatment of dermatitis, peptic ulcer, or rheumatoid arthritis. In another embodiment, the present invention does not encompass the treatment of respiratory diseases that do not develop into pulmonary fibrosis.

Therapeutic Compositions and Formulations

The present invention also provides for therapeutic or pharmaceutical compositions comprising a compound of the invention in a form that can be combined with a pharmaceutically acceptable carrier. In this context, the compound may be, for example, isolated or substantially pure. The present invention also embodies nutritional supplements and health food or drink formulations comprising a compound of the invention.

The term "carrier" refers to a diluent, adjuvant, excipient, or vehicle with which the compound is administered. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers, particularly for injectable solutions. Particularly preferred pharmaceutical carriers for treatment of or amelioration of inflammation in the central nervous system are carriers that can penetrate the blood/brain barrier. As used herein carriers do not include the natural plant material as it exists in nature.

Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The therapeutic composition, if desired, can also contain minor amounts of wetting or emulsifying agents, or pH buffering agents. These compositions can take the feu in of solutions, suspensions, emulsion, tablets, capsules, powders, sustained-release formulations and the like. The composition can be formulated with traditional binders and carriers such as triglycerides. Examples of suitable pharmaceutical carriers are described in "Remington's Pharmaceutical Sciences" by E. W. Martin. Such compositions contain a therapeutically effective amount of the therapeutic composition, together with a suitable amount of carrier so as to provide the form for proper administration to the patient. The formulation should suit the mode of administration.

In preferred embodiments, the compositions are prepared in a form adapted for delivery into the lungs. For instance, the liquid pharmaceutical composition may be lyophilized prior to use in pulmonary delivery, where the lyophilized composition is milled to obtain the finely divided dry powder consisting of particles within a desired size range noted above. For another instance, spray-drying may be used to obtain a dry powder form of the liquid pharmaceutical composition, and the process is carried out under conditions that result in a substantially amorphous finely divided dry powder consisting of particles within the desired size range. For methods of preparing dry powder forms of pharmaceutical compositions, see, for example, WO 96/32149; WO 97/41833; WO 98/29096; and U.S. Pat. Nos. 5,976,574; 5,985,248; 6,001, 336; and 6,875,749 herein incorporated by reference. In addition, the dry powder form of the pharmaceutical composition may be prepared and dispensed as an aqueous or nonaqueous solution or suspension, in a metered-dose inhaler.

In addition, a pharmaceutically effective amount of the dry powder form of the composition may be formulated as an aerosol or other preparation suitable for pulmonary inhalation. The amount of dry powder form of the composition placed within the delivery device is sufficient to allow for delivery of a pharmaceutically effective amount of the composition to the subject by inhalation. The delivery device delivers, in a single or multiple fractional doses, by pulmonary inhalation a pharmaceutically effective amount of the composition to the subject's lungs. The aerosol propellant may be any conventional material employed for this purpose.

When used in the context of pharmaceutical compositions suitable for pulmonary delivery, these terms have the following intended meaning. By "aqueous" is intended a composition prepared with, containing, or dissolved in water, including mixtures wherein water is the predominating substance in the mixture. By "nonaqueous" is intended a composition prepared with, containing, or dissolved in a substance other than water or mixtures wherein water is not the predominating substance in the mixture. By "solution" is intended a homogeneous preparation of two or more substances, which may be solids, liquids, gases, or intercombinations thereof. By "suspension" is intended a mixture of substances such that one or more insoluble substances are homogeneously dispersed in another predominating substance.

For purposes of the present invention, the terms "solid" and "dry powder" are used interchangeably with reference to the pharmaceutical compositions. By "solid" or "dry powder" form of a pharmaceutical composition is intended the composition has been dried to a finely divided powder having a moisture content below about 10% by weight, usually below about 5% by weight, and preferably below about 3% by weight. This dry powder form of the composition consists of particles comprising the peptides of the subject invention. Preferred particle sizes are less than about 90.0 μm mean diameter, more preferably less than about 70.0 μm, more preferably less than about 50.0 μm even more preferably about less than about 30.0 μm, more preferably less than about 10.0 μm, more preferably less than about 7.0 μm, even more preferably in the range of 0.1 to 5.0 μm, most preferably in the range of about 1.0 to about 5.0 μm diameter.

A surfactant may be added to the pharmaceutical composition to reduce adhesion of the dry powder to the walls of the delivery device from which the aerosol is dispensed. Suitable surfactants for this intended use include, but are not limited to, sorbitan trioleate, soya lecithin, and oleic acid. Devices suitable for pulmonary delivery of a dry powder form of a composition as a nonaqueous suspension are commercially available. Examples of such devices include the Ventolin metered-dose inhaler (Glaxo Inc., Research Triangle Park, N.C.) and the Intal Inhaler (Fisons, Corp., Bedford, Mass.). See also the aerosol delivery devices described in U.S. Pat. Nos. 5,522,378; 5,775,320; 5,934,272; and 5,960,792 herein incorporated by reference.

In yet another embodiment, the pharmaceutical composition can be delivered in a controlled release system. In one embodiment, a pump may be used (see Langer, supra; Sefton, 1987, CRC Crit. Ref Biomed. Eng. 14:201; Buchwald et al., 1980, Surgery 88:507; and Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., 1985, Science 228:190; During et al., 1989, Ann. Neurol. 25:351; Howard et al., 1989, J. Neurosurg. 71:105). In yet another embodiment, a controlled release system can be placed in proximity of the composition's target, i.e., the lung, thus requiring only a fraction of the systemic dose (see, e.g., Goodson, in Medical Applications of Controlled Release, supra, vol. 2, pp. 115-138 (1984).

In one embodiment, the composition is formulated in accordance with routine procedures as a pharmaceutical composition adapted for local injection administration to human beings. Typically, compositions for local injection administration are solutions in sterile isotonic aqueous buffer. Where necessary, the composition may also include a solubilizing agent and a local anesthetic such as lidocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile water for injection or saline can be provided so that the ingredients may be mixed prior to administration.

The therapeutic or pharmaceutical compositions of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The present invention also provides for the modification of the compound such that it is more stable once administered to a subject, i.e., once administered it has a longer time period of effectiveness as compared to the unmodified compound. Such modifications are well known to those of skill in the art, e.g., microencapsulation, etc.

The invention also provides a pharmaceutical pack or kit comprising one or more containers filled with one or more of the ingredients, e.g., compound, carrier, of the pharmaceutical compositions of the invention.

The compounds of the present invention can also be formulated consistent with traditional Chinese medicine practices. The composition and dosage of the formulation that are effective in the treatment of a particular disease, condition or disorder will depend on the nature of the disease, condition or disorder by standard clinical techniques.

The traditional Chinese medicine in prescription amounts can be readily made into any form of drug, suitable for administering to humans or animals. Suitable forms include, for example, tinctures, decoctions, and dry extracts. These can be taken orally, applied through venous injection or mucous membranes. The active ingredient can also be formulated into capsules, powder, pallets, pastille, suppositories, oral solutions, pasteurized gastroenteric suspension injections, small or large amounts of injection, frozen powder injections, pasteurized powder injections and the like. All of the above-mentioned methods are known to people skilled in the art, described in books and commonly used by practitioners of herbal medicine.

A tincture is prepared by suspending herbs in a solution of alcohol, such as, for example, wine or liquor. After a period of suspension, the liquid (the alcohol solution) may he administered, for example, two or three times a day, one teaspoon each time.

A decoction is a common form of herbal preparation. It is traditionally prepared in a clay pot, but can also be prepared in glass, enamel or stainless steel containers. The formulation can be soaked for a period of time in water and then brought to a boil and simmered until the amount of water is reduced by, for example, half An extract is a concentrated preparation of the essential constituents of a medicinal herb. Typically, the essential constituents are extracted from the herbs by suspending the herbs in an appropriate choice of solvent, typically, water, ethanol/water mixture, methanol, butanol, iso-butanol, acetone, hexane, petroleum ether or other organic solvents. The extracting process may be further facilitated by means of maceration, percolation, repercolation, counter-current extraction, turbo-extraction, or by carbon-dioxide hypercritical (temperature/pressure) extraction. After filtration to rid of herb debris, the extracting solution may be further evaporated and thus concentrated to yield a soft extract (extractum spissum) and/or eventually a dried extract, extracum siccum, by means of spray drying, vacuum oven drying, fluid-bed drying or freeze-drying. The soft extract or dried extract may be further dissolved in a suitable liquid to a desired concentration for administering or processed into a form such as pills, capsules, injections, etc.

Routes of Administration

The compounds and compositions of the subject invention can be administered to the subject being treated by standard routes, including oral, inhalation, or parenteral administration including intravenous, subcutaneous, topical, transdermal, intradermal, transmucosal, intraperitoneal, intramuscular, intracapsular, intraorbital, intracardiac, transtracheal, subcutaneous, subcuticular, intraarticular, subcapsular, subarachnoid, intraspinal, epidural and intrasternal injection, infusion, and electroporation, as well as co-administration as a component of any medical device or object to be inserted (temporarily or permanently) into a subject.

In preferred embodiments, the compounds and compositions of the subject invention are administered in any route suitable for pulmonary delivery. Pulmonary administration requires dispensing of the biologically active substance from a delivery device into a subject's oral cavity during inhalation. For purposes of the present invention, pharmaceutical compositions can be administered via inhalation of an aerosol or other suitable preparation that is obtained from an aqueous or nonaqueous solution or suspension form, or a solid or dry powder form of the pharmaceutical composition, depending upon the delivery device used. Pulmonary inhalation results in deposition of the inhaled composition in the alveoli of the subject's lungs. Once deposited, the compounds or compositions may be absorbed, passively or actively, across the alveoli epithelium and capillary epithelium layers into the bloodstream.

The amount of the therapeutic or pharmaceutical composition of the invention which is effective in the treatment of a particular disease, condition or disorder will depend on the route of administration, and the seriousness of the disease, condition or disorder, and should be decided according to the judgment of the practitioner and each patient's circumstances. In general, the dosage ranges from about 0.001 mg/kg to about 3 g/kg. For instance, suitable unit dosages may be between about 0.01 to about 3 g, about 0.01 to about 1 g, about 0.01 to about 500 mg, about 0.01 to about 400 mg, about 0.01 to about 300 mg, about 0.01 to about 200 mg, about 0.01 to about 100 mg, about 0.01 to about 50 mg, about 0.01 to about 30 mg, about 0.01 to about 20 mg, about 0.01 to about 10 mg, about 0.01 to about 5 mg, about 0.01 to about 3 mg about, 0.01 to about 1 rng, or about 0.01 to about 0.5 mg. Such a unit dose may be administered more than once a day, e.g. two or three times a day.

The amount of active ingredient that may be combined with the carrier materials to produce a single dosage form will vary, depending such as the type of the condition and the subject to be treated. In general, a therapeutic composition contains from about 5% to about 95% active ingredient (w/w). More specifically, a therapeutic composition contains from about 20% (w/w) to about 80% or about 30% to about 70% active ingredient (w/w).

Once improvement of the patient's condition has occurred, a maintenance dose is administered if necessary. Subsequently, the dosage or the frequency of administration, or both, may be reduced as a function of the symptoms to a level at which the improved condition is retained. When the symptoms have been alleviated to the desired level, treatment should cease. Patients may however require intermittent treatment on a long-term basis upon any recurrence of disease symptoms.

In addition, in vitro assays may optionally be employed to help identify optimal dosage ranges. The precise dose to be employed in the formulation will also depend on the route of administration, and the seriousness of the disease, condition or disorder, and should be decided according to the judgment of the practitioner and each patient's circumstances. Effective doses may be extrapolated from dose-response curves derived from in vitro or animal model test systems.

Following are examples that illustrate procedures for practicing the invention. These examples should not be construed as limiting.

EXAMPLE 1

Induction of Inflammatory Responses by IR

Briefly, C57BL/6 fibrosis-prone mice were exposed to IR at 0, 5, or 9 Gy. As shown in FIG. 1, IR induces a first surge in inflammatory responses 6 hours after exposure, a second surge 4-10 days after exposure, and a third surge 180 days aftr exposure (IL2 only) (FIG. 1, first lane: normal control). FIG. 2 shows surges of IM levels in C57BL/6 and C3H/NeH mice with IR-induced traumatic brain injury (TBI) 6 hr, 1, 2, 4, and 10 days after exposure at 9 Gy. This indicates that IR induces inflammatory responses and the levels of inflammatory mediators can be used to monitor IR-induced lung injury.

EXAMPLE 2

Modulation of Inflammatory Responses During the Acute Phase of IR-Induced Pneumonitis This Example demonstrates that GA suppresses the surge in inflammatory responses during the acute phase of IR-induced pneumonitis, which occurs within 48 hours after IR exposure to mice. Briefly, C57BL/6 fibrosis-prone mice received a single-dose of thoracic IR at 15 Gy with a dose rate of 1.9 Gy/min. Six hours after IR exposure, the mice were divided into the following treatment groups: 1) normal (received 0 Gy; no treatment); 2) vehicle-treated; 3) GA-treated (30-40 mg/kg/q.o.d) (i.e. every other day) (the GA dosage used herein was derived from the effective dosage for humans (3-4 mg/kg), which is typically 6-10 times lower than that of mice); 4) dexamethasone-treated (Positive Control 1) (Dex, 3 mg/kg, i.m. or p.o. qod); 5) amifostine-treated (Positive Control 2) (Ami, 200 mg/kg/ i.v, 0.5 hr prior to irradiation); and 6) celebrex-treated (Positive Control 3) (30 mg/kg, po, qod).

The mice were sacrificed 2.5 days after IR exposure, and fresh lung tissue homogenates were prepared using lysis buffer mixed with protenase inhibitor cocktails. After protein concentration was adjusted to 1 mg/ml, the fresh lung homogenates were added to ELISA plates at a concentration of 100 μl/well. The levels of inflammatory mediators were measured by ELISA.

As shown in FIG. 3, IR exposure causes a surge in the levels of inflammatory mediators (IMs), including IL1a, TNFa, PF4 and VCAM-1. GA effectively reduced levels of IMs, as compared to the vehicle-treated mice (FIG. 2, $p<0.05$). The extent of inhibition by GA was comparable to that of celebrex, dexamethasone and amifostine.

EXAMPLE 3

Suppression of Plasma Exudation and Inflammatory Cell Infiltration During the Acute Phase of IR-Induced Pneumonitis This Example demonstrates that GA suppresses IR-induced plasma exudation and inflammatory cell infiltration during the acute phase of IR-induced pneumonitis. Briefly, C57BL/6 fibrosis-prone mice received a single-dose of thoracic IR at 15 Gy with a dose rate of 1.9 Gy/min and were treated as described in Example 2. The mice were sacrificed 2.5 days after IR exposure, and lung tissues were harvested and analyzed for morphological changes.

Figure 4:
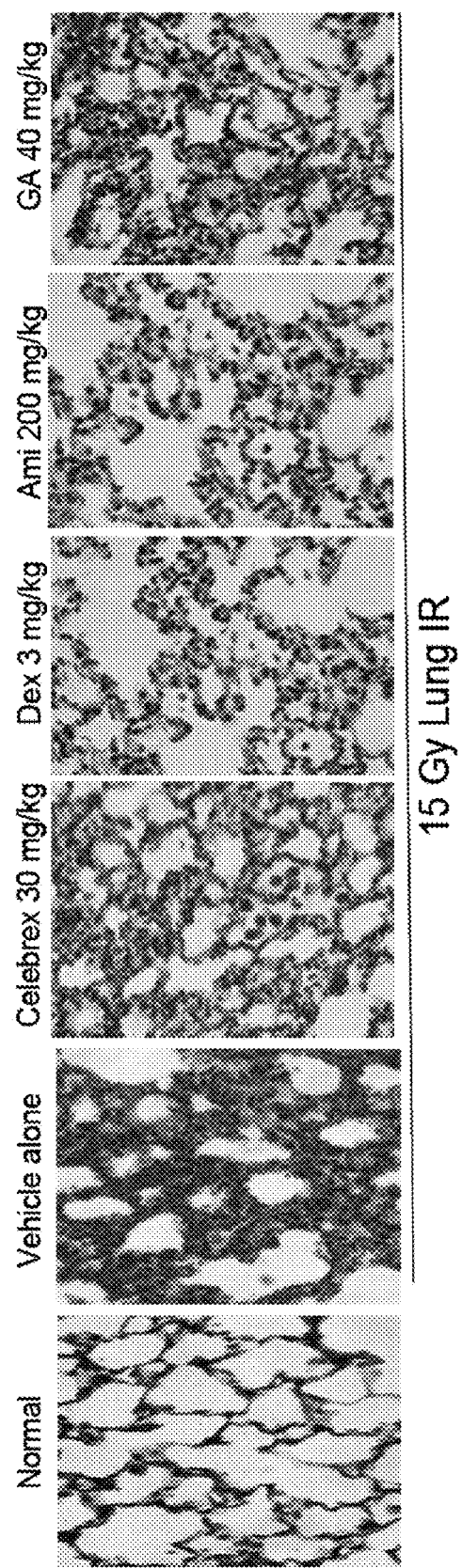
FIG. 4 shows that GA reduces inflammatory cell infiltration and plasma exudation into the interstitial space during the acute phase of IR-induced pneumonitis (2.5 days after exposure to thoracic IR at 15 Gy).

As shown in FIG. 4, the vehicle-treated lungs were filled with infiltrated inflammatory cells and plasma exudates, as compared to non-IR-exposed normal lungs. GA potently suppressed plasma exudation and inflammatory cell infiltration into the interstitial space. Celebrex, dexamethasone and amifostine also produced similar treatment effects.

EXAMPLE 4

Reduction by Plasma Levels of SP-D and IL1a During the Acute Phase of IR-Induced Pneumonitis This Example demonstrates that GA reduced plasma levels of SP-D and IL1a. IR damages lung epithelium and endothelium cells, and causes dysfunction of tight junction, increased cellular permeability, and the loss of integrity of the alveolar-capillary barrier. As a result, SP-D and IL1a abnormally enter into the blood from inflamed pulmonary tissue, leading to elevated plasma levels of SP-D and IL1a.

Figure 5A:
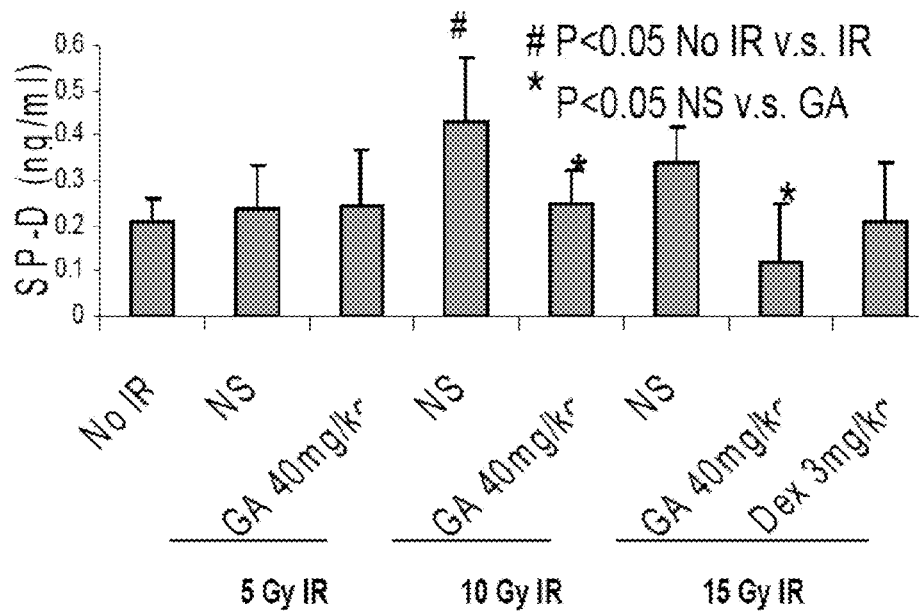
FIG. 5 shows that GA reduces plasma levels of SP-D and ILa during the acute phase of IR-induced pneumonitis.
Figure 5B:
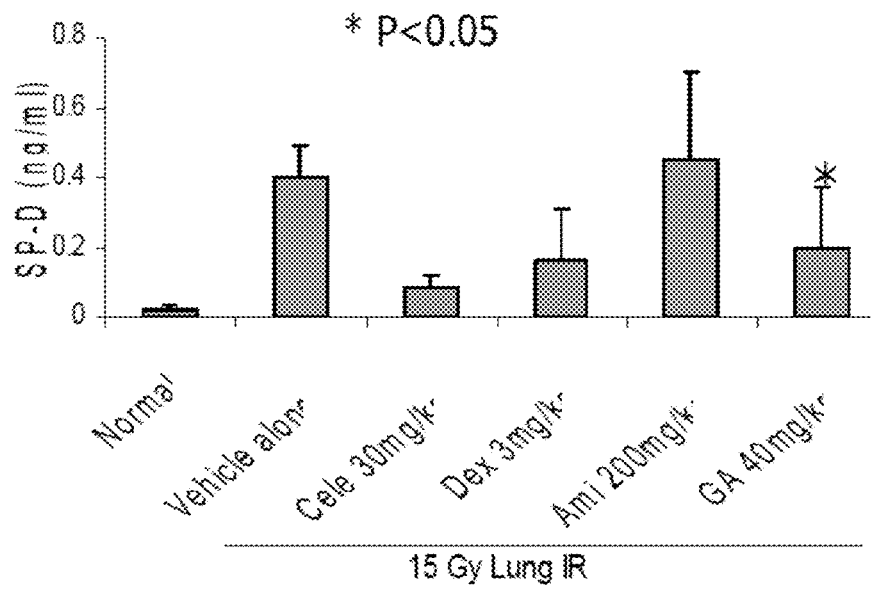
Figure 5C:
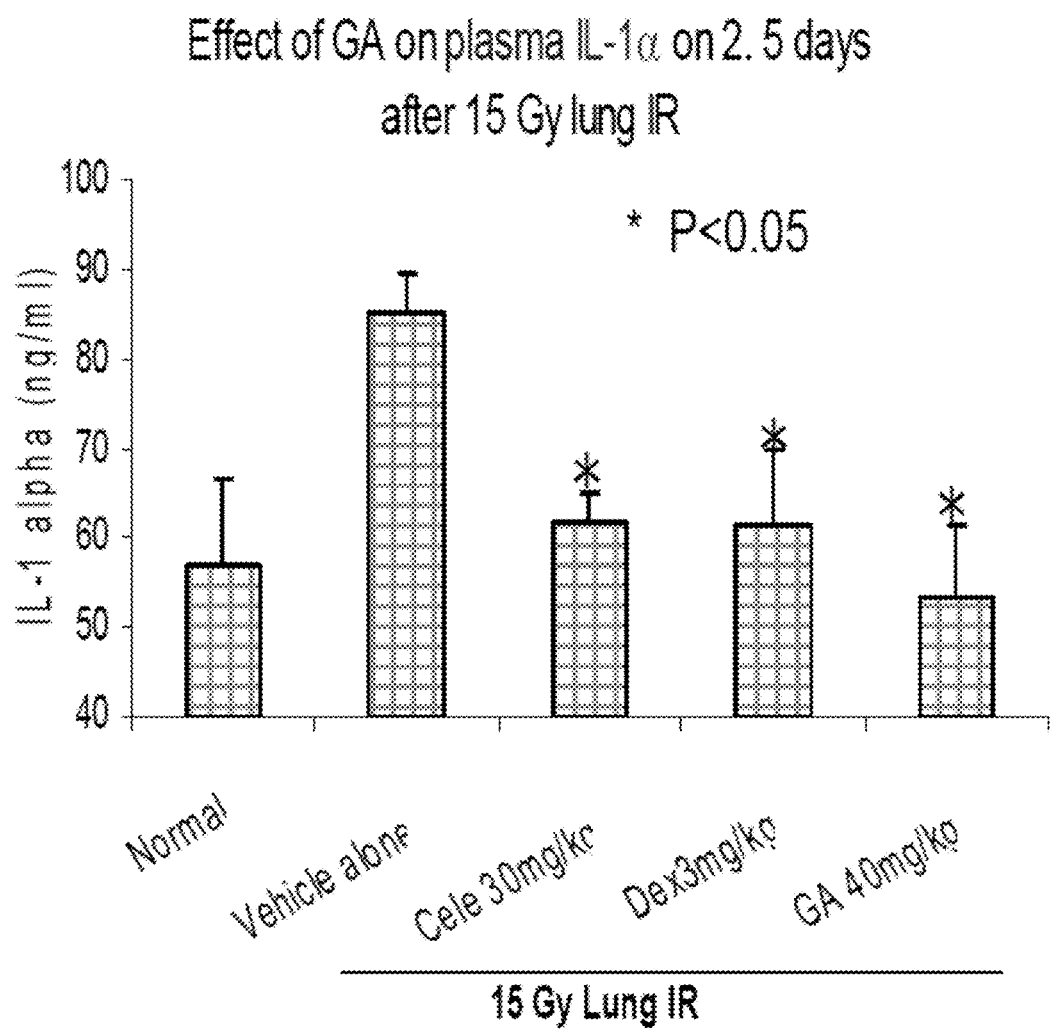

In this Example, C57BL/6 fibrosis-prone mice received a single-dose of thoracic IR at 15 Gy with a dose rate of 1.9 Gy/min and were treated as described in Example 2. The mice were sacrificed 2.5 days after IR exposure, and plasma levels of SP-D and IL1a were measured. FIG. 5A shows that IR exposure results in a dose-dependent increase in plasma levels of SP-D. Specifically, plasma SP-D did not increase under IR exposure at 5 Gy, but increased at 10 Gy and 15 Gy. As shown in FIGS. 5A-B, GA effectively reduced plasma levels of SP-D ($P<0.05$). In addition, FIG. 5C shows that GA effectively reduced plasma levels of IL1a ($P<0.05$).

EXAMPLE 5

Effects of GA on the Sub-Acute Phase of IR-Induced Pneumonitis

This Example demonstrates that GA effectively modulates the sub-acute phase of IR-induced pneumonitis, which occurs about 2-4 weeks after IR exposure to the mice. Briefly, C57BL/6 fibrosis-prone mice received a thoracic IR and were treated as described in Example 2. The mice were sacrificed 17 days after IR exposure, and lung tissues were harvested. Bronchoalveolar lavage fluid (BALF) assays were performed.

Figure 6A:
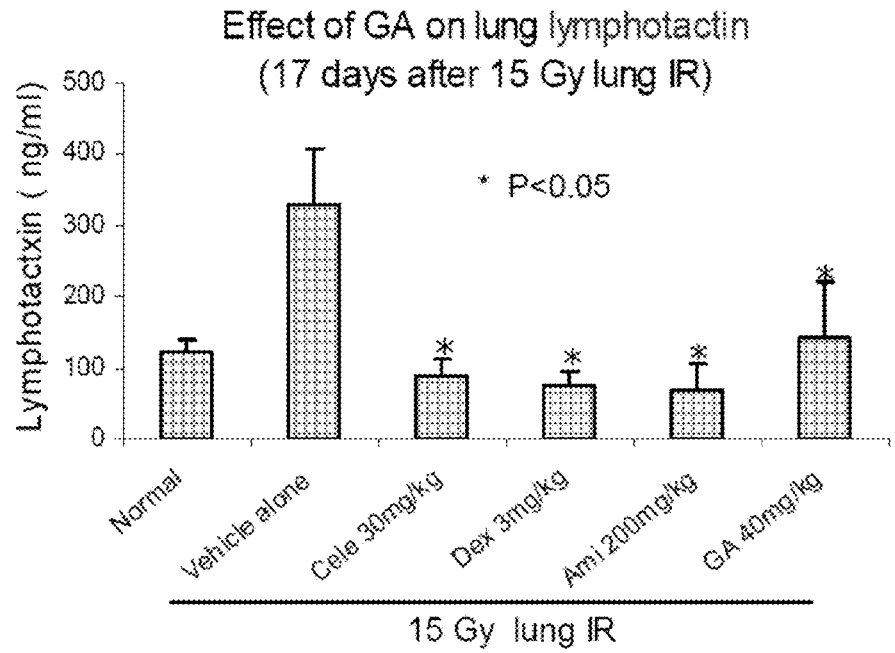
FIG. 6 shows that GA reduces the levels of inflammatory mediators during the sub-acute phase of IR-induced pneumonitis (17 days post IR exposure).
Figure 6B:
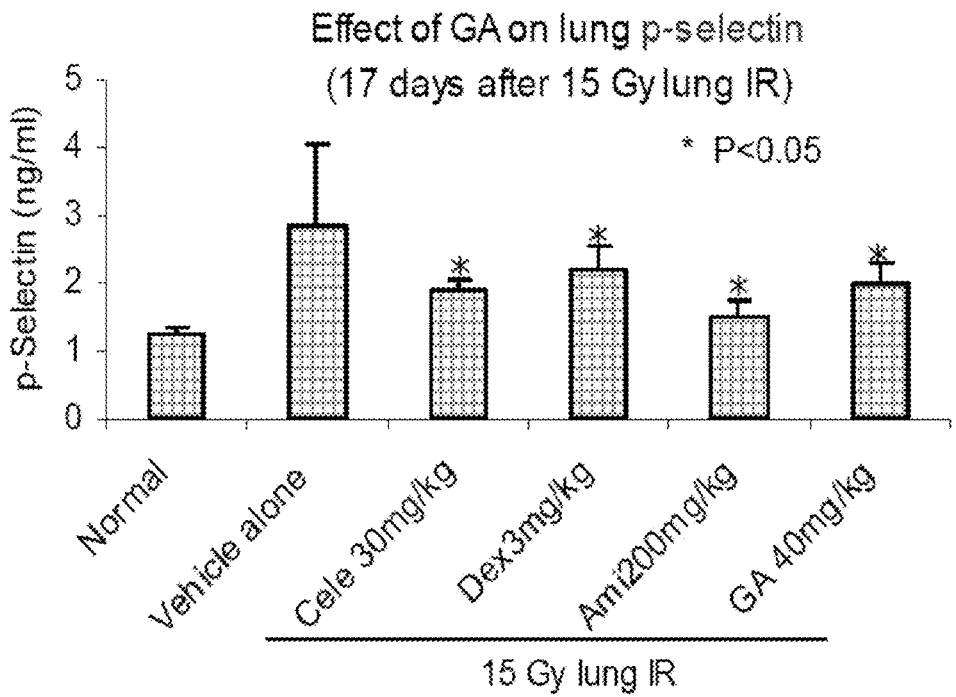
Figure 7A:
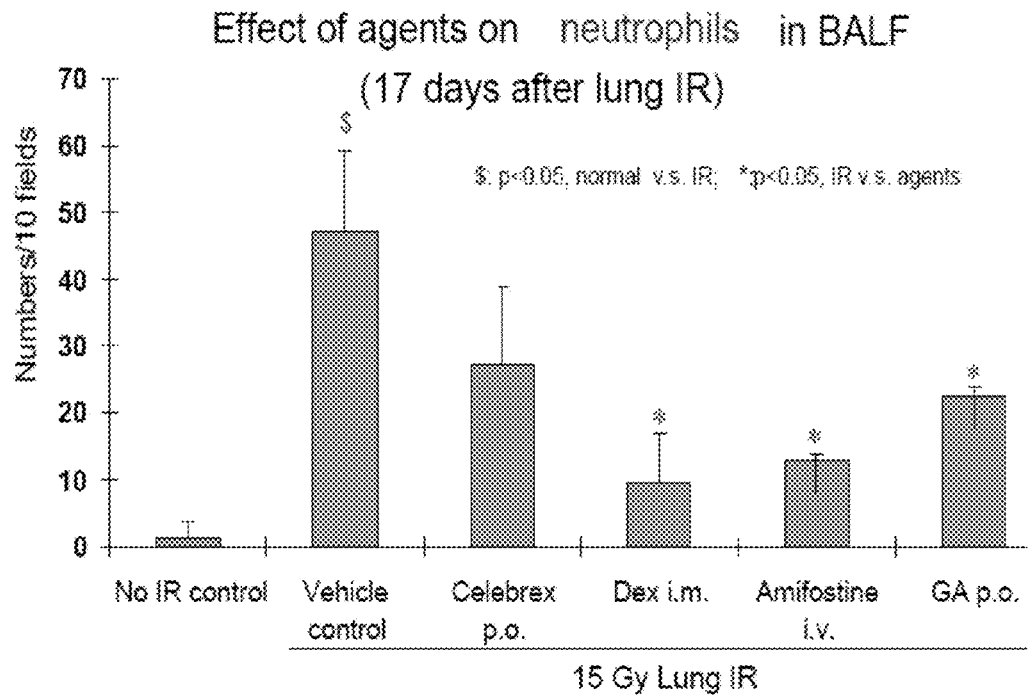
FIG. 7 shows that GA reduces the number of neutrophils and myeloperoxidase (MPO) activity in bronchoalveolar lavage fluid (BALF) during the sub-acute phase of IR-induced pneumonitis (17 days post IR exposure at 15 Gy).
Figure 7B:
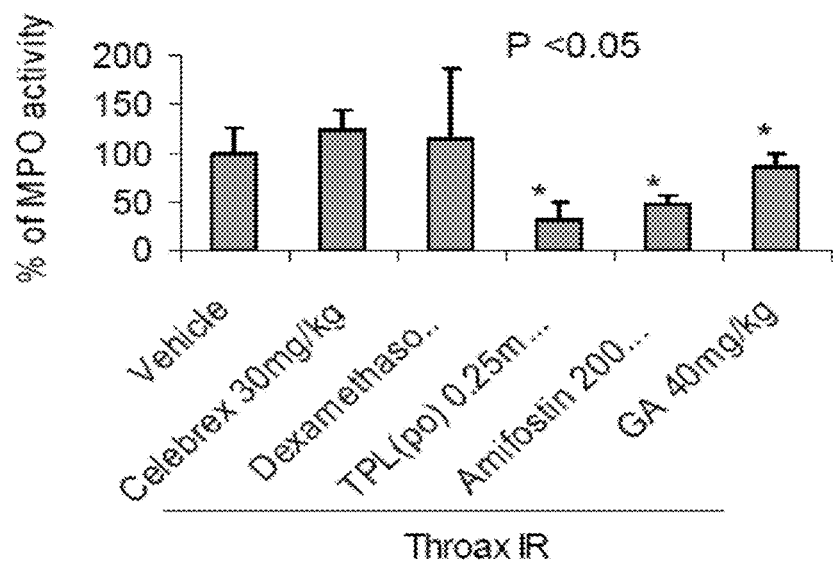
Figure 8:
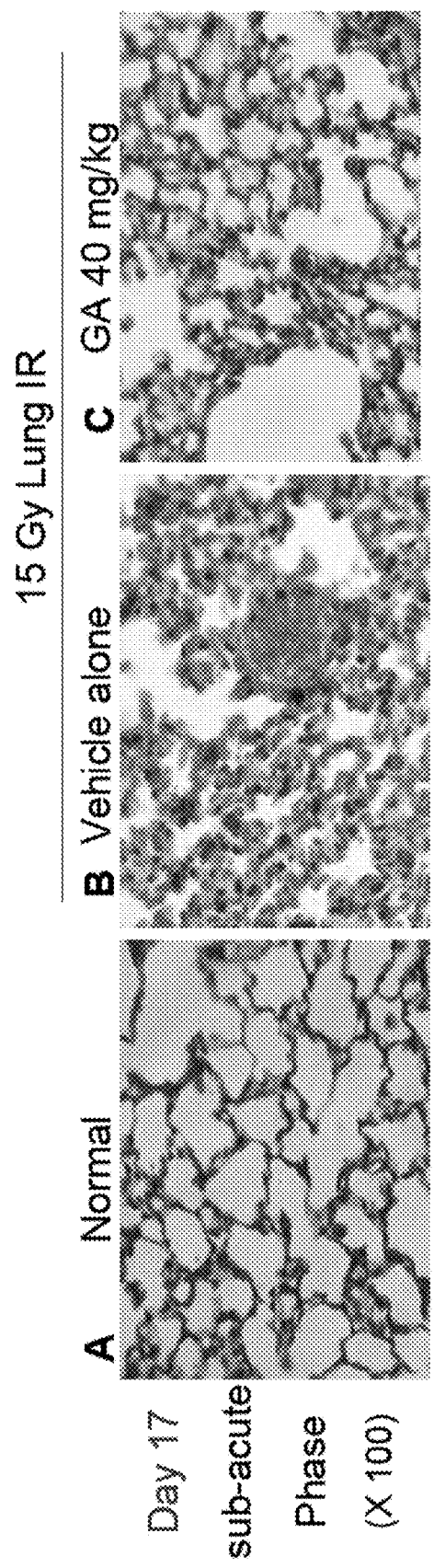
FIG. 8 shows that GA mitigates the sub-acute phase of IR-induced pneumonitis (17 days post IR exposure at 15 Gy).
Figure 9A:
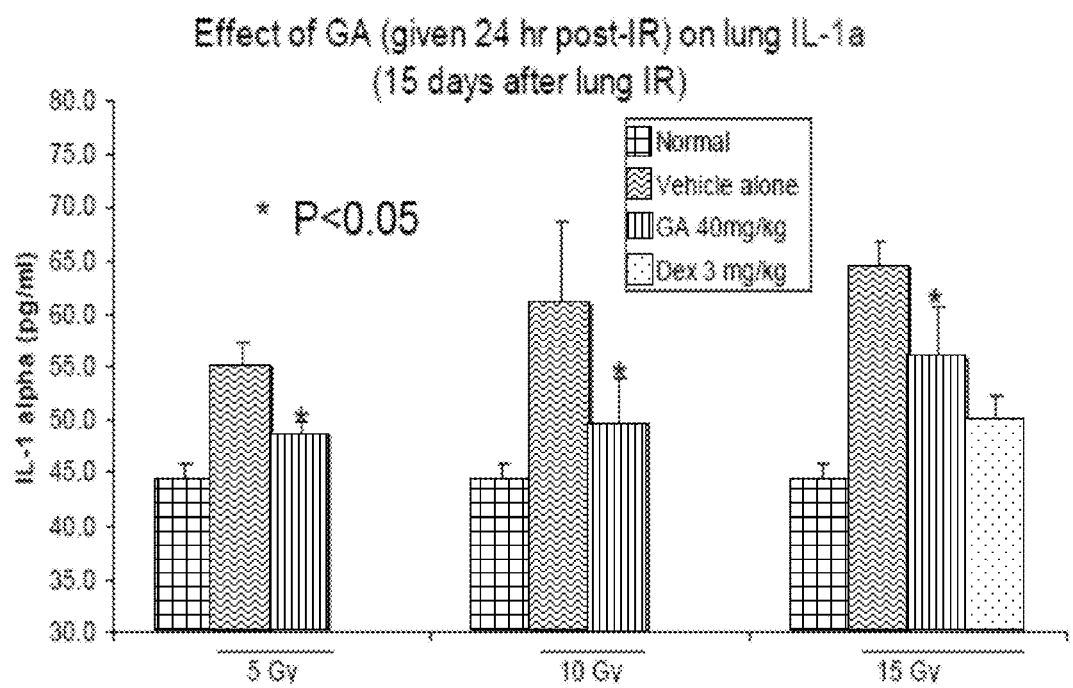
FIG. 9 shows that GA inhibits inflammatory responses during the sub-acute phase of IR-induced pneumonitis. GA was administered to mice 24 hours post IR exposure at 15 Gy.
Figure 9B:
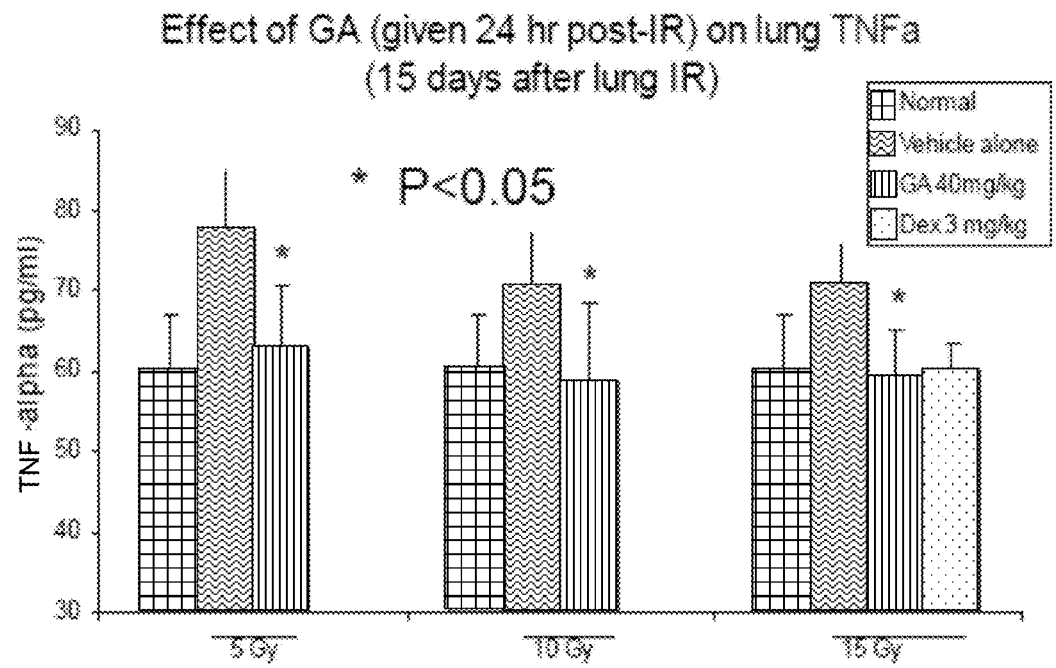
Figure 9C:
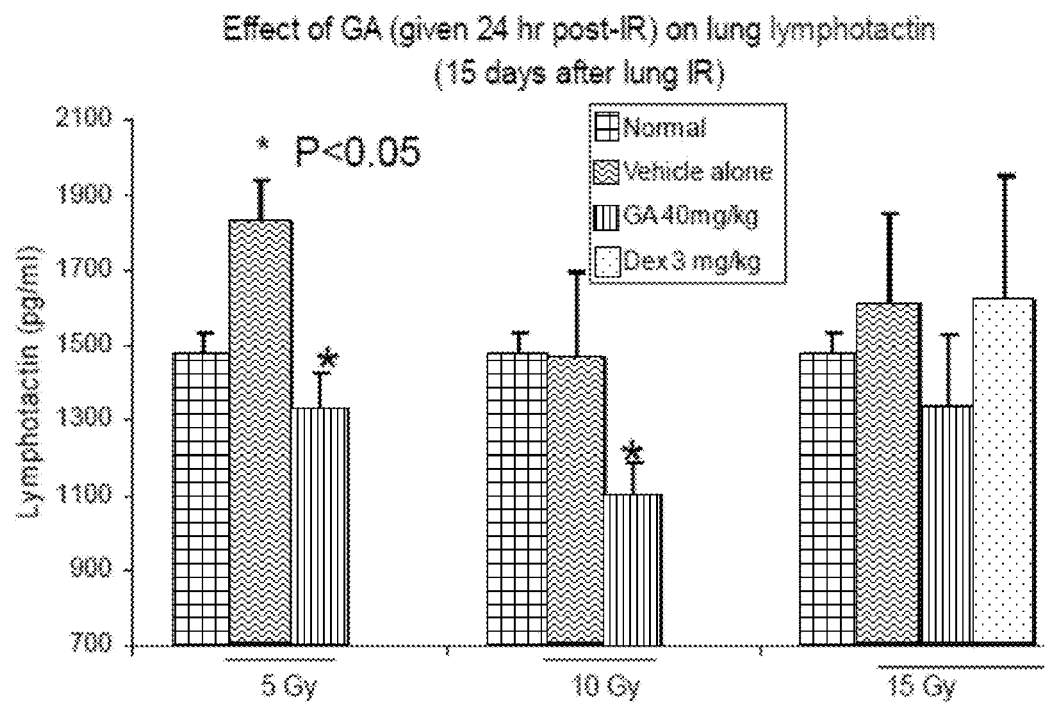
Figure 9D:
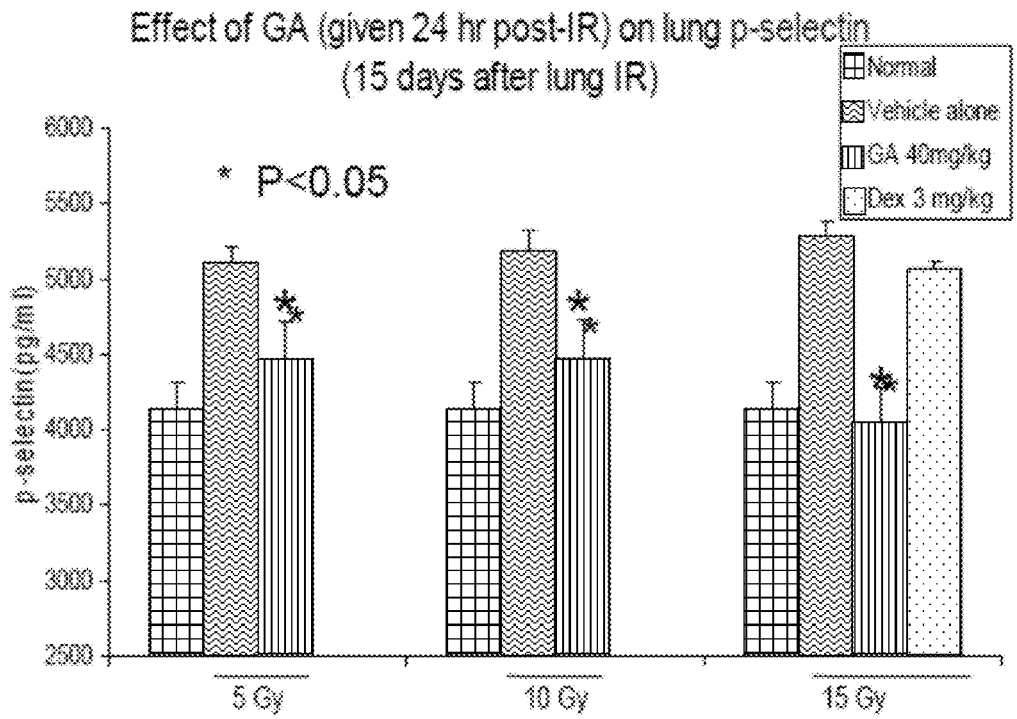

The results showed that GA reduced the levels of lymphotactin and p-selectin, two key inflammatory mediators involved in pulmonary immune responses and innate immunity (FIGS. 6A and B, $P<0.05$). In addition, GA reduced the level of neutrophils infiltrated into the bronchoalveolar lavage fluid (FIG. 7A, $P<0.05$). GA also reduced myeloperoxidase (MPO) activity in (BALF) (FIG. 7B, $P<0.05$). FIG. 8A-C also shows the suppression of infiltration of neutrophils into the interstitial fluid (FIGS. 8A-C).

In addition, it is observed that the surge of inflammatory mediators during the sub-acute phase does not exhibit a dose-dependent manner. IR exposure at 5 Gy can trigger inflammatory responses. The present inventors have also observed that IR exposure any level higher than 5 Gy may trigger pulmonary fibrosis. The larger the dose is, the faster it may take for fibrosis to develop. The present inventors have observed that mice treated with IR at 7.5 Gy developed pulmonary fibrosis and died of lung failure 1.5 years after IR exposure.

The administration of GA 24 hours after IR exposure can effectively block the surge in inflammatory responses. FIG. 9 shows that GA potently reduced the levels of key inflammatory mediators including IL1a, TNFa, lymphotactin and p-selectin in mice exposed to thoracic IR at 5, 10 and 15 Gy, respectively.

EXAMPLE 6

Attenuation Effects of GA on IR-Induced Pulmonary Fibrosis

This Example demonstrates that GA improves lung function and attenuates IR-induced pulmonary fibrosis. Mice exposed to thoracic IR develops pulmonary fibrosis 6 months after IR exposure at 18 Gy, 8 months after IR exposure at 15 Gy, and 10 months after IR exposure at 12.5 Gy. To access the treatment effects of GA on lung fibrosis and lung function, the respiratory rate, lung density, and lung compliance of the mice were determined.

To assess improvement on respiratory function, mice exposed to thoracic IR at 15 Gy were treated with GA (30-40 mg/kg) q.o.d. or twice/week for 3 months. Mouse respiratory rate was measured using a Harvard rodent ventilator connected to a pressure plethysmograph. As shown in FIGS. 10A-B, IR exposure significantly increased mouse respiratory rate, which was effectively reduced by GA treatment ($P<0.05$).

Figure 11:
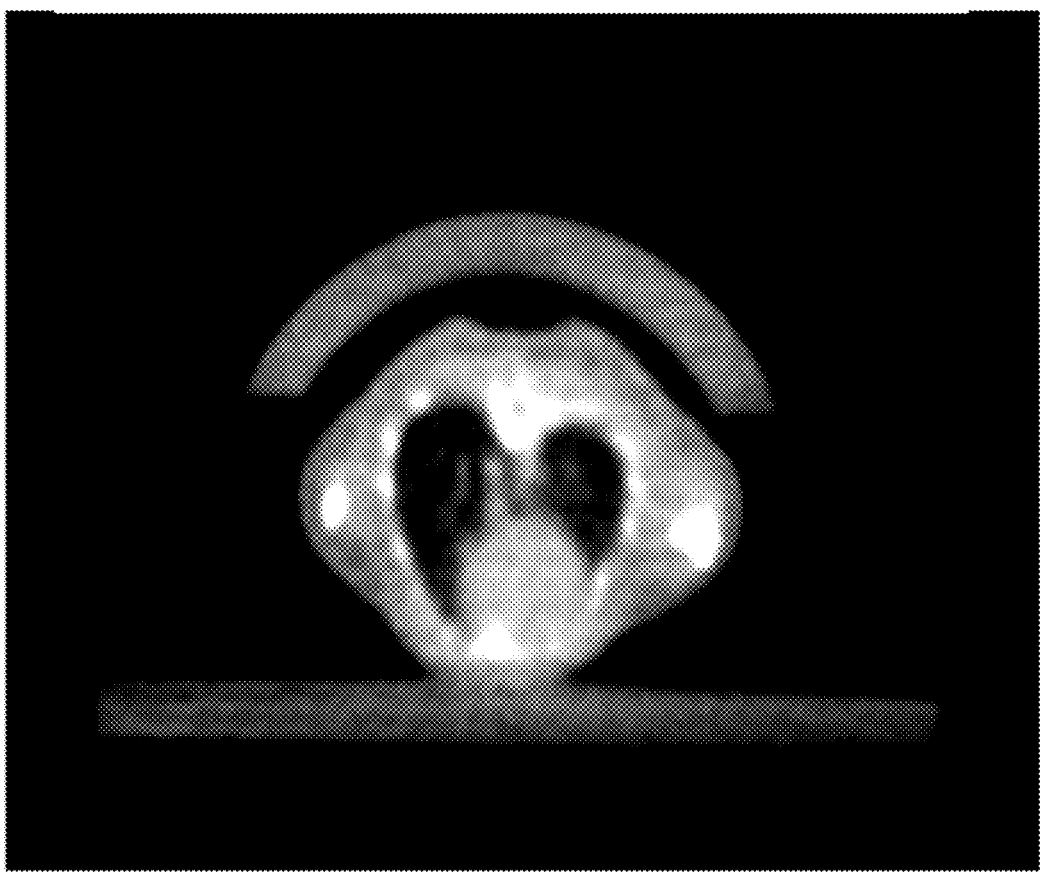
FIG. 11 shows Cone Beam Computed Topography (CBCT) image of mouse lung.

To assess effects of GA on lung density, cone beam CT scan (CBCT) of mouse lungs was performed. CBCT provides a complete 3D 650×650×428 scan (i.e. 428 slices) of the lungs with isotropic resolution at 270 μm (central slice shown in FIG. 11) in 30 seconds. The scanner achieves a CT density sensitivity of ~5 $HU^3$, and thus, changes in lung density can be discerned.

Figure 12A:
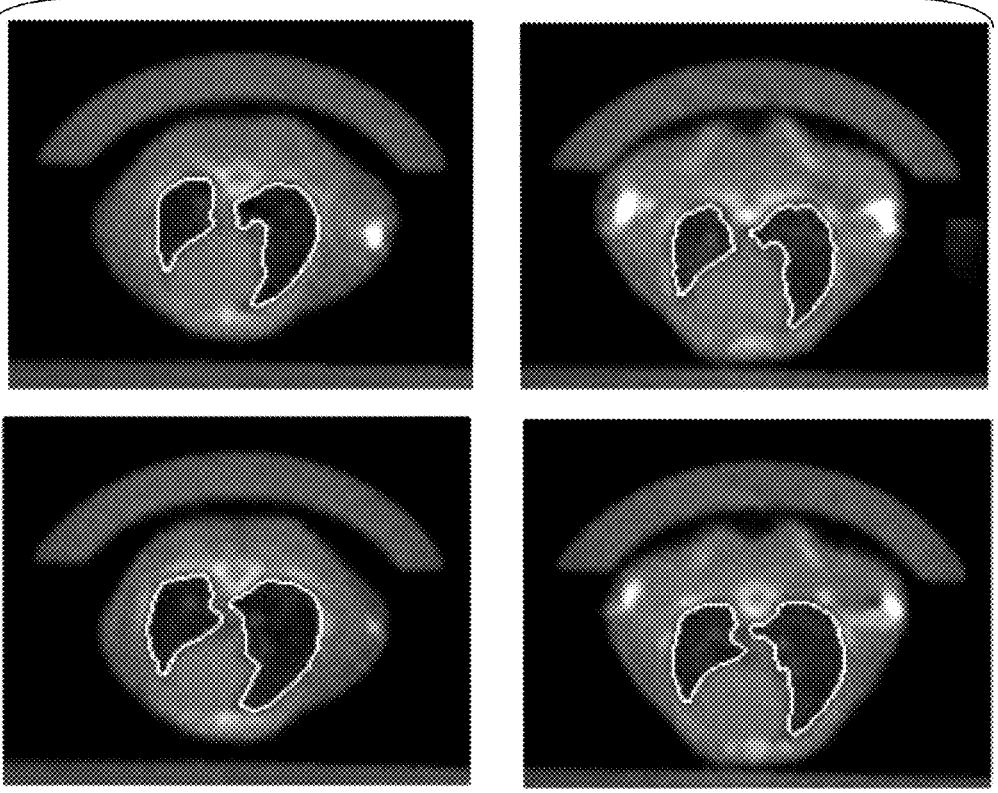
FIG. 12 shows CBCT images of mouse lungs.
Figure 12B:
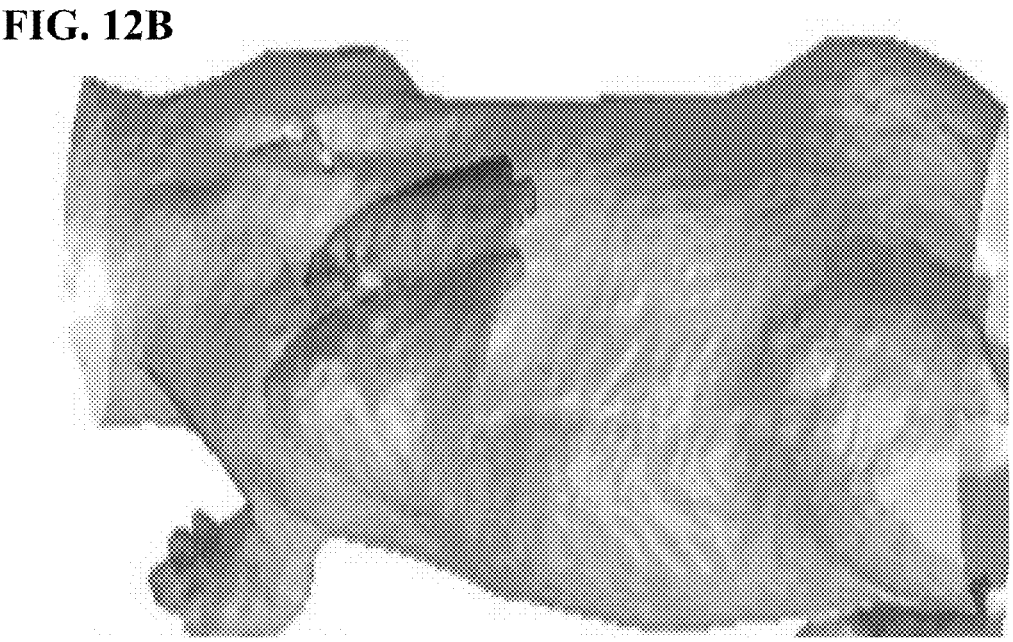
Figure 13:
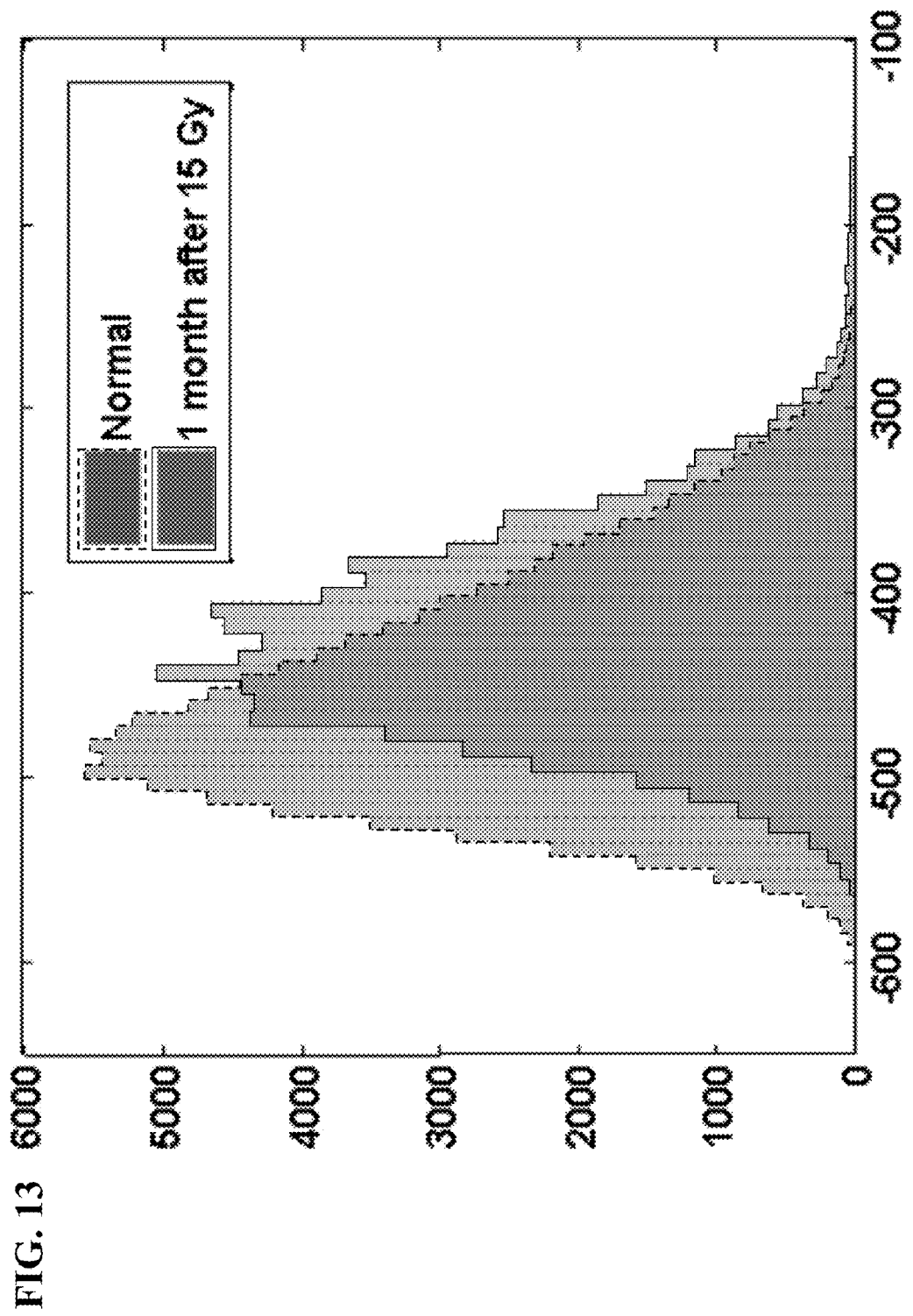
FIG. 13 shows increases in lung density as a result of IR exposure. The lung density of normal (non-IR exposed) control mouse is shown in dotted lines. The lung density of the mouse 1 month after exposure to thoracic IR at 15 Gy is shown in solid lines.

The CBCT imaging data were further analyzed using MATLAB software. The lungs were automatically segmented (FIG. 12A) and a 3D image was generated for each mouse lung (FIG. 12B). To reduce the effect of cardiac motion on the mean value of lung density, boundaries of the lungs were not used for analysis. A histogram of voxel intensity (pulmonary tissue density) of each mouse was created (FIG. 13).

Table 1 shows the mean value and standard deviation (SD) of lung density. 1R exposure at 18 Gy gradually increased lung density from a normal density of −454+60 HU (Noun's field) to as high as −364+45 HU in a year. As shown in FIG. 14, GA significantly reduced the abnormal increase in lung density ($P<0.05$). The reduction in lung density by GA is more potent that of celebrex.

TABLE 1

Comparison of Lung Density of Mice in Different Treatment Groups

| Group | Mean Density (HU) | Standard Deviation (HU) |
|---|---|---|
| Normal Control | −454 | 60 |
| 1 month post IR exposure at 15 Gy | −420 | 56 |
| 1 year post IR exposure at 18 Gy | −364 | 45 |
| 1 year post IR exposure at 18 Gy with GA treatment | −458 | 88 |

To assess the effects of GA on lung compliance, mice were anesthetized and their trachea were surgically exposed and incised. An 18-gauge, 1 cm stainless steel tube was inserted into the trachea and secured with surgical sutures. The respiratory rate and tidal volume of the mice were measured by a Harvard rodent ventilator. The average respiratory rate was 150 breaths per minute and the tidal volume was adjusted according to the weight (0.01 ml per gram body weight). The mice were then placed in a plethysmograph for pressure-volume measurements. As shown in FIG. 15, GA treatment potently, and mostly effectively, enhanced lung compliance, which was decreased by IR exposure ($P<0.05$).

EXAMPLE 7

Reduction of Fibrotic Conditions

This Example demonstrates that GA reverses pathological alteration of lung tissues, improves lung morphology, and suppresses collagen deposition in IR-induced fibrosis. Briefly, mice treated with GA (40 mg/kg/q.o.d.) for 3 months were sacrificed 7 months after IR exposure at 15 Gy, and lung tissue specimens were stained using hematoxylin and eosin (H&E) stain. As shown in FIG. 16, the vehicle-treated lungs exhibited disruption of normal lung structure, including thickening of alveolar walls and increased fibroblast levels. In comparison, the GA-treated lungs exhibited near-normal morphology (FIG. 16).

To assess whether GA reduces abnormal collagen deposition in lungs, lung tissue specimen was stained with collagen-binding trichrome blue dye. FIG. 17 shows that GA reduces collagen deposition caused by IR exposure and improves lung morphology.

The reduction of collagen deposition was further analyzed by measuring the levels of hydroxyproline, a key component of collagen. FIG. 18A shows that GA reduced hydroxyproline levels in the lungs, as compared to IR +vehicle control ($P<0.05$). FIG. 18B shows that GA reduced the level of TGFβ, a pro-fibrotic factor.

EXAMPLE 8

Low Toxicity

This Example demonstrates that long-term use of GA causes little side effects, based on observations of the activity, fur morphology and body weight (BW) of treated mice. Specifically, 7.5 months post IR exposure at 15 Gy, the vehicle-treated mice lost 6-7 grains of body weight, whereas less severe loss of BW was observed in GA- or celebrex-treated mice (FIG. 19). No mouse died during GA treatment.

EXAMPLE 9

Effect of GA on the Endocrine System

The chemical structure of GA is similar to that of cortisol. Thus, this Example investigates whether the long-term use of GA would affect the production of cortisol and cause side effects. The plasma levels of ACTH (adrenocorticotropic hormone), a cortisol-releasing hormone, were measured using ELISA at Weeks 6, 7, and 10 after GA-treatments (40 mg/kg, god, p.o). The results (data not shown) showed that while GA reduced ACTH levels by 60% at Week 6, ACTH levels rapidly returned to normal throughout Weeks 7-10. In comparison, dexamethasone treatment caused a 10-50-fold reduction in ACTH levels throughout Weeks 7-10.

In addition, plasma levels of growth hormone (GH) were measured using ELISA at Weeks 6, 7, and 10 after GA treatments. The results showed that both GA and dexamethasone increased plasma GH level. It has been reported that IR exposure abnormally reduces growth hormone level, and thus, GA-induced increase in GH level is beneficial for patient recovery[4].

EXAMPLE 10

Treatment Effects of GLA on IR-Induced Pneumonitis

In collaboration with radiation oncologists at the First Affiliated Hospital of Fujian Medical School in China, GLA tablets (produced by Minophagen Co. in Japan and available in pharmacies in China) were administered to a patient who received her $2^{nd}$ IR treatment for lung cancer. In her $1^{st}$ IR treatment, the patient developed severe IR-induced pneumonitis three months after IR treatment, and exhibited symptoms of pulmonary injury, including fever, cough and shortness of breath. To control the progression of pneumonitis, she received dexamethasone treatment. Due to tumor re-growth 9 months after her $1^{st}$ IR treatment, she received a $2^{nd}$ IR treatment with warnings that IR may worsen pneumonitis.

In order to mitigate IR-induced lung injury, GLA was administered at a does of 150 mg per day (equivalent to GA about 85 mg per day) starting from the date of $2^{nd}$ treatment for 3 months. The result was unexpectedly surprising. The patient, whose pneumonitis was expected to worsen, did not exhibit any symptom of pneumonitis or fibrosis during the course of GLA treatment. A comparison of the CT results taken from the $1^{st}$ and $2^{nd}$ IR treatments also showed that GLA significantly reduced lung density in the patient (FIG. 20).

It should be understood that the examples and embodiments described herein are for illustrative purposes only and that various modifications or changes in light thereof will be suggested to persons skilled in the art and are to be included within the spirit and purview of this application and the scope of the appended claims.

All references, including publications, patent applications and patents, cited herein are hereby incorporated by reference to the same extent as if each reference was individually and specifically indicated to be incorporated by reference and was set forth in its entirety herein.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The description herein of any aspect or embodiment of the invention using clients such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

REFERENCES

1. Tsoutsou, P. G. & Koukourakis, M. I. Radiation pneumonitis and fibrosis: mechanisms underlying its pathogenesis and implications for future research. Int J Radiat Oncol Biol Phys 66, 1281-1293 (2006).
2. Choi, N. C. Radioprotective effect of amifostine in radiation pneumonitis. Semin Oncol 30, 10-17 (2003).
3. Ning, R., Tang, X., Conover, D. & Yu, R. Flat panel detector-based cone beam computed tomography with a circle-plus-two-arcs data acquisition orbit: preliminary phantom study. Medical Physics 30, 1694-1705 (2003).
4. Vazquez et al., Protective effect of enriched diet plus growth hormone administration on radiation-induced intestinal injury and on its evolutionary pattern in the rat, Digestive Diseases and Sciences, 44 (11) 2350-2058 (1999).

We claim:

1. A method of treating or ameliorating pulmonary fibrosis induced by radiation, wherein said method comprises administering, to a subject that receives at least 1 Gy radiation and is in need of such treatment, an effective amount of an isolated compound or a salt thereof, wherein said compound is selected from the group consisting of:

(A) glycyrrhetinic acid (GA);
(B) glycyrrhizic acid (GLA);
(C) ester, ether and/or amide forms of glycyrrhetinic acid (GA), represented by the following structure (Structure C):

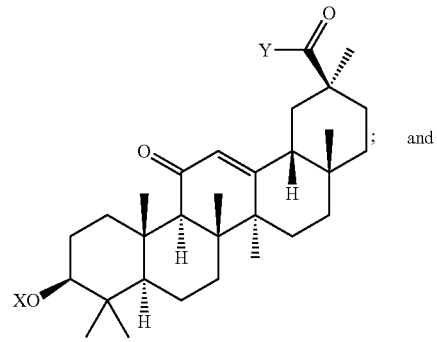

and (D) ester and/or amide forms of glycyrrhizic acid (GLA), represented by the following structure (Structure D):

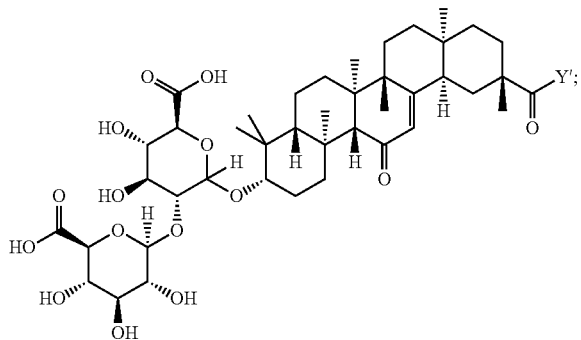

wherein

X is selected from the group consisting of
a) alkyl, substituted alkyl, alkenyl, substituted alkenyl, —COOH, acyl, alkylcarbonyl, benzyl, cyclic alkyl, and cyclic alkenyl;
b) an acid group selected from the group consisting of acetic acid, carboxylic acid, aspartic acid, formic acid, citric acid, benzoic acid, hippuric acid, malic acid, mucic acid, phosphoric acid, sulfuric acid, gluconic acid, maleic acid, succinic acid, tartaric acid, and lactic acid; and
c) a carbohydrate moiety; and each of Y and Y' is —NH$_2$, alkylamino, or alkoxy.

2. The method, according to claim 1, wherein the subject is a human.

3. The method, according to claim 1, wherein the compound is glycyrrhetinic acid (GA) or a salt thereof.

4. The method, according to claim 1, wherein the compound is glycyrrhizic acid (GLA) or a salt thereof.

5. The method, according to claim 1, wherein the subject has been diagnosed with pulmonary fibrosis.

6. The method, according to claim 1, wherein the subject receives radiation therapy for cancer treatment.

7. The method, according to claim 1, wherein the subject receives accidental exposure to radiation.

8. The method, according to claim 1, wherein the level of an inflammatory mediator in lung tissue of the subject is reduced, wherein said inflammatory mediator is selected from the group consisting of SP-D, IL1α, TNFα, IL6, PF4, P-selectin, L-selectin, VCAM-1, lymphotactin, and prostaglandin E (PGE).

9. The method, according to claim 1, wherein the content of collagen, fibronectin, proteoglycan and/or hydroxyproline in lung tissue of the subject is reduced.

10. The method, according to claim 1, wherein the level of TGFβ in lung tissue of the subject is reduced.

11. The method, according to claim 1, wherein respiratory rate of the subject is reduced, lung density of the subject is reduced, and/or lung compliance of the subject is increased.

12. The method, according to claim 1, wherein the compound is administered after the subject receives said at least 1 Gy radiation.

13. The method, according to claim 1, wherein the subject receives radiation at a dose of at least 1 Gy in a day.

14. The method, according to claim 1, wherein the method consists of administering the compound to a subject who is at risk of developing pulmonary fibrosis.

15. A method of treating or ameliorating pulmonary injury induced by radiation, wherein said method comprises administering, to a subject that receives at least 1 Gy radiation and is in need of such treatment, an effective amount of an isolated compound or a salt thereof, wherein said compound is selected from the group consisting of:

(A) glycyrrhetinic acid (GA);
(B) glycyrrhizic acid (GLA);
(C) ester, ether and/or amide forms of glycyrrhetinic acid (GA), represented by the following structure (Structure C):

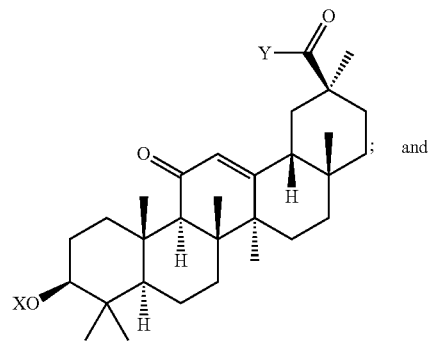

(D) ester and/or amide forms of glycyrrhizic acid (GLA), represented by the following structure (Structure D):

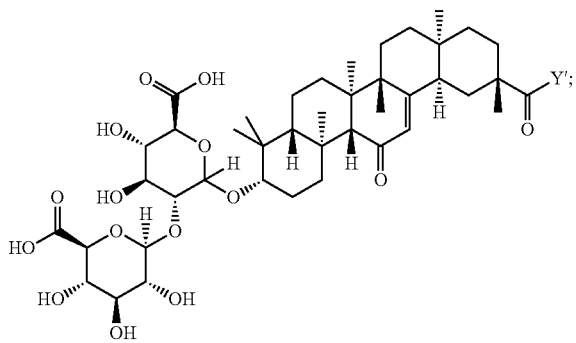

wherein

X is selected from the group consisting of
a) alkyl, substituted alkyl, alkenyl, substituted alkenyl, —COOH, acyl, alkylcarbonyl, benzyl, cyclic alkyl, and cyclic alkenyl;
b) an acid group selected from the group consisting of acetic acid, carboxylic acid, aspartic acid, formic acid, citric acid, benzoic acid, hippuric acid, malic acid, mucic acid, phosphoric acid, sulfuric acid, gluconic acid, maleic acid, succinic acid, tartaric acid, and lactic acid; and
c) a carbohydrate moiety; and each of Y and Y' is —NH$_2$, alkylamino, or alkoxy.

16. The method, according to claim 15, wherein the compound is glycyrrhetinic acid (GA) or a salt thereof.

17. The method, according to claim 15, wherein the compound is glycyrrhizic acid (GLA) or a salt thereof.

18. The method, according to claim 15, wherein the subject receives radiation at a dose of at least 1 Gy in a day.

19. The method, according to claim 15, wherein the compound is administered after the subject receives said at least 1 Gy radiation.

20. A method of treating or ameliorating pulmonitis induced by radiation, wherein said method consists of administering, to a subject that receives at least 1 Gy radiation and is in need of such treatment, an effective amount of an isolated compound or a salt thereof, wherein said compound is selected from the group consisting of:

(A) glycyrrhetinic acid (GA);

(B) glycyrrhizic acid (GLA);

(C) ester, ether and/or amide forms of glycyrrhetinic acid (GA), represented by the following structure (Structure C):

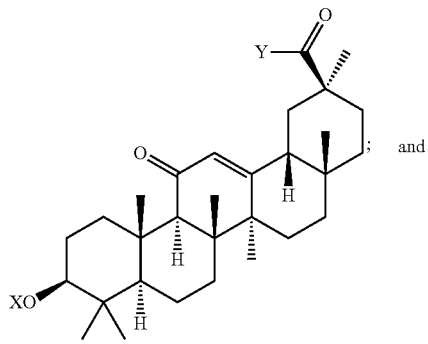

and (D) ester and/or amide forms of glycyrrhizic acid (GLA), represented by the following structure (Structure D):

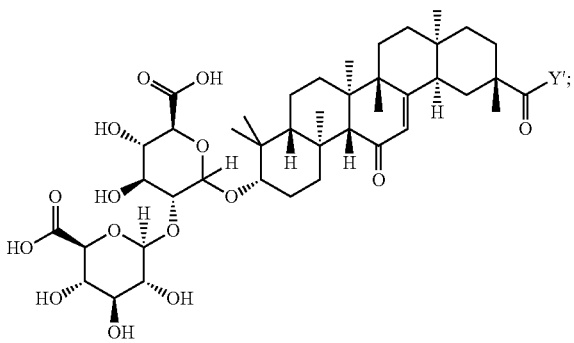

wherein
X is selected from the group consisting of
a) alkyl, substituted alkyl, alkenyl, substituted alkenyl, —COOH, acyl, alkylcarbonyl, benzyl, cyclic alkyl, and cyclic alkenyl;
b) an acid group selected from the group consisting of acetic acid, carboxylic acid, aspartic acid, formic acid, citric acid, benzoic acid, hippuric acid, malic acid, mucic acid, phosphoric acid, sulfuric acid, gluconic acid, maleic acid, succinic acid, tartaric acid, and lactic acid; and
c) a carbohydrate moiety; and
each of Y and Y' is —$NH_2$, alkylamino, or alkoxy.

21. The method, according to claim 20, wherein the method consists of administering the compound to a subject who is at risk of developing pulmonitis.

\* \* \* \* \*